United States Patent [19]

DePinto

[11] Patent Number: 5,269,313
[45] Date of Patent: Dec. 14, 1993

[54] FILTER AND METHOD FOR FILTERING BASELINE WANDER

[75] Inventor: Victor M. DePinto, Kirkland, Wash.
[73] Assignee: Sherwood Medical Company, St. Louis, Mo.
[21] Appl. No.: 756,415
[22] Filed: Sep. 9, 1991
[51] Int. Cl.$^5$ .......................................... A61B 5/0428
[52] U.S. Cl. ...................................... 128/696
[58] Field of Search ................ 128/696, 702–706, 128/901–902

[56] References Cited

U.S. PATENT DOCUMENTS

| | | | |
|---|---|---|---|
| 3,569,852 | 3/1971 | Berkovits | 128/696 |
| 3,822,696 | 7/1974 | Ekstrom et al. | 128/703 |
| 3,923,041 | 12/1975 | Stasz et al. | 128/2.06 R |
| 4,170,227 | 10/1979 | Feldman et al. | 128/704 |
| 4,192,318 | 3/1980 | Dam et al. | 128/708 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,537,201 | 8/1985 | Delle-Vedove et al. | 128/697 |
| 4,563,704 | 1/1986 | Hirota | 358/167 |
| 4,658,831 | 4/1987 | Reinhard et al. | 128/697 |
| 4,664,116 | 5/1987 | Shaya et al. | 128/419 PT |
| 4,793,361 | 12/1988 | DuFault | 128/696 |
| 4,802,491 | 2/1989 | Cohen et al. | 128/702 |
| 4,812,976 | 3/1989 | Lundy | 364/413.06 |
| 4,908,579 | 3/1990 | Tawfik et al. | 328/167 |
| 4,914,398 | 4/1990 | Jove et al. | 328/167 |
| 4,931,743 | 6/1990 | Fukuda et al. | 328/167 |
| 4,947,858 | 8/1990 | Smith | 128/696 |
| 5,025,794 | 6/1991 | Albert et al. | 128/696 |
| 5,107,849 | 4/1992 | Bellin et al. | 128/696 |

FOREIGN PATENT DOCUMENTS 210148 of 0000 Fed. Rep. of Germany .
1-227740 9/1989 Japan .

OTHER PUBLICATIONS

Taylor et al., "Medical & Biological Engineering", Jul., 1974, vol. 12, No. 4, pp. 493–502.
Kirber et al., "Proceedings of the 10th Annal Northwest", Bioengineering Conference, Hanover, N.H., Mar. 15–16, 1982, pp. 217–221.
"A Filter to Suppress ECG Baseline Wander and Pressure ST-Segment Accuracy in a Real-time Environment" by Roddy A. Frankel, Eric W. Pottala, Richard W. Bowser, and James J. Bailey, October issue of *Journal of Electrocardiology*, pp. 316 through 317.
"Digital Filters for ECG Signals" by David W. Mortara, 1977 Computers in Cardiology Proceedings, pp. 512 through 514.
"ECG Baseline Wander Reduction Using Linear Phase Filters" by J. A. van Alste et al., published in Computers and Biomedical Research, 19, 417–427 (1986).
"Electrocardiogram Baseline Noise Estimation and Removal Using Cubic Splines and State-Space Computation Techniques" by C. R. Myer and H. N. Keiser, published in *Computers and Biomedical Research*, 10, 459, 4–470 (1977).
IRE Transactions on Circuit Thertory, vol. 18, No. 6, Nov. 1971, New York, US, pp. 659–664, Thiran, "Recursive Digital Filters with Maximally Flat Group Delay".

*Primary Examiner*—William E. Kamm
*Attorney, Agent, or Firm*—Andrew J. Beck; Montgomery W. Smith; Curtis D. Kinghorn

[57] ABSTRACT

A linear phase high pass filter having a linear phase low pass filter in parallel with an electronic delay means is disclosed to remove baseline wander from an ECG signal. The linear phase low pass filter is preferably a digital Infinite Impulse Response (IIR) filter. An input ECG signal is simultaneously presented to an IIR low pass filter and an electronic delay. The low pass filter passes the low frequency baseline signal while blocking the ECG signal comprised of higher frequency components than the cutoff frequency of the low pass filter. Thereafter, the outputs from the IIR low pass filter and delay are passed to a summer that subtracts the output of the low pass filter from the output of the delay to produce the output of the filter. The combination of the output of a low pass filter being subtracted from a delayed input signal produces a high pass filter. The resulting high pass filter has a −0.3 dB cutoff frequency of about 0.5 Hertz while providing a virtually constant group delay for the ECG signal passed through the filter.

20 Claims, 21 Drawing Sheets

| Stage | unit delay gain |
|---|---|
| A | 51.04049843 |
| B | 356.17391298 |
| C | 963.764706115 |

| coefficient | Realized value |
|---|---|
| 1A1 | 0.980407714844 |
| 1B0 | 1.0 |
| 2A1 | 0.967300415039 |
| 2A2 | 0.970108032227 |
| 2B0 | 0.029922485316 |
| 3A1 | 0.961685180664 |
| 3A2 | 0.962722778320 |
| 3B0 | 0.125 |

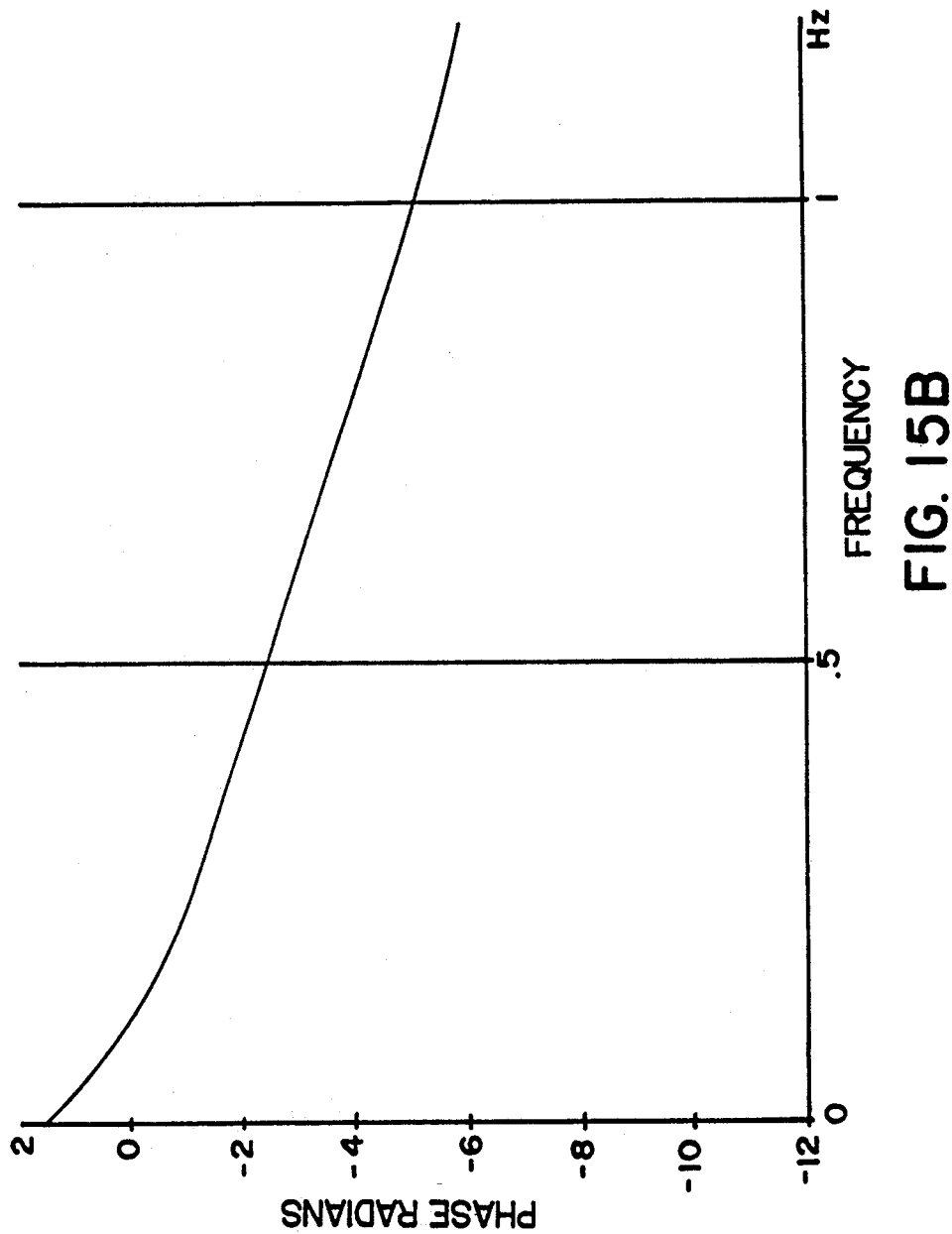

FILTER AND METHOD FOR FILTERING BASELINE WANDER

BACKGROUND OF THE INVENTION

1. Field of the Invention

The instant invention relates to a filter for filtering baseline wander from an ECG signal and more specifically to a linear phase high pass digital filter for filtering baseline wander from an ECG signal.

2. Description of Related Art

ECG traces are produced by detecting electrical impulses present in the heart and converting these electrical signals into a visually discernible form such as a trace written by a pen on a moving paper or a trace displayed on a video display screen. The electrical signals of the heart are detected by placing electrodes on the skin of the patient which electrodes are sensitive to the electrical potentials generated by the heart as the heart goes through its beating cycle. The potentials generated by the heart are usually quite small. These heart generated potentials detected by the electrodes have typical amplitudes of only a few millivolts so that any stray electrical potentials can either mask the heart-generated potentials or shift them. This masking or shifting makes proper analysis of the ECG signal difficult or impossible.

One particular kind of extraneous electrical potential is caused by electrode-skin interaction. This interaction occurs where acids naturally present in the skin react with metals in the electrode in an electrolytic reaction which causes an effective "battery" to be formed. This "battery" provides a relatively constant long term or D.C. signal which varies only slightly over time. This particular phenomena is known in the art as "baseline wander". An example of an ECG signal having baseline wander is shown in FIG. 1.

Four general groups of solutions have been devised to deal with the baseline wander problem. First, special electrodes are used made of silver or silver chloride. These electrodes are less reactive to the acids in the skin than other types of electrodes and therefore minimize the electrolytic reaction with the resulting unwanted electrical potentials.

Another solution to the baseline wander problem is to abrasively remove the top layer of skin. This top layer produces the acids which ultimately produce the electrolytic reaction with the electrodes. Removal of the top layer of skin is typically done by using an electrode having an abrasive surface which surface abrades the top layer of skin. Thereafter, the electrode is ground into the skin. Because the top layer of skin is essentially removed, the amount of acid present to react with the electrode to cause the electrolytic reaction is reduced.

Another solution to the baseline wander problem is to convert the ECG signal to a digital signal and then estimate the baseline wander of the ECG signal on a computing device by creating a cubic spline which passes through the P-R segment of every beat. The cubic spline is then used to determine an offset to be added to the ECG signal to cancel the baseline wander. The P-R segment of each beat must be identified in real time by the computing device. The disadvantage of the cubic spline method is that if the P-R segment is not correctly identified, the method will fail and may cause even more baseline distortion than was originally present.

Finally, the last group of solutions dealing with the baseline wander problem is to use a high pass filter to remove the slowly varying signals such as those created by the electrolytic reaction manifested as baseline wander. Ideally, these filters pass all frequencies above about 0.5 Hertz, since baseline wander typically occurs with frequencies below this frequency and the energy in the ECG signal is mostly above this frequency.

In the simplest form, a single pole high pass filter is used, such as that shown schematically in FIG. 2, comprising a capacitor connected between the input and the output of the filter and a resistor located on the output side of the capacitor biasing the capacitor to ground.

As is well known in the art, any complex signal can be represented as the combination of sinusoidal signals at varying frequencies and amplitudes. The series of sinusoidal signals is called a Fourier series. If a single pole high pass filter is used to create a $-3$ dB cutoff frequency of 0.5 Hertz, as is shown in the graph of FIG. 3A, the corresponding inherent phase shift of the frequencies of the input signal passed through the filter is severely shifted for frequencies above the cutoff frequency as shown in FIG. 3B. The phase shift inherent in a single pole filter manifests itself in a delay in the passage of Fourier series component frequencies of the ECG signal through the filter. The delay is defined as the negative of the rate of phase change divided by the frequency of interest. The amount of delay in such single pole high pass filters varies depending on the frequency of the component parts passed through the filter as shown in FIG. 3C. These delays of varying amounts depending on the frequency of the ECG signal passed through the high pass filter cause the shape of the entire ECG signal to become distorted which distortion hinders analysis of the ECG signal.

The most severe problem with single pole high pass filters with a cutoff frequency of about 0.5 Hz, whether analog or digital, is that the single pole filter inherently depresses the ST segment of the ECG signal. However, the ST segment is diagnostically significant. If this segment is distorted, the doctor will have difficulty in correctly analyzing the ECG signal.

In order to avoid this severe phase shift with its attendant distortion of the ECG signal and depression of the ST segment, the typical single pole filter used as a baseline wander filter has its cutoff frequency moved from about 0.5 Hertz down to about 0.05 Hertz as shown in FIG. 4A. When the cutoff frequency of the filter is moved to about 0.05 Hz, the phase shift of the ECG signal for frequencies above about 0.5 Hz approaches zero as shown in FIG. 4B. The corresponding delay for the ECG signal approaches zero above about 0.5 Hz as shown in FIG. 4C. In this case, the severe phase shift which occurs at about the cutoff frequency, that is around 0.05 Hz, does not affect any frequency components of the ECG signal which occur at higher frequencies than 0.5 Hz. Because the ECG signal has virtually no frequency components below about 0.5 Hz, the amount of distortion of the ECG signal by the filter is minimized.

The problem with using a filter having a cutoff frequency of about 0.05 Hz is that baseline wander often occurs at frequencies above 0.05 Hertz, particularly in the range of 0.05 Hz to 0.5 Hz, so that a single pole filter with a cutoff frequency of 0.05 Hz is not as effective of a filter of these baseline wander signals as is desired. These single pole filters may be implemented as analog or digital filters as is well understood in the art.

More complicated filters having a plurality of poles and zeros could be used to create a baseline wander filter having a cutoff frequency of about 0.5 Hz and a near constant delay for the ECG signal passed through the filter in order to reduce distortion caused by the filtering of the ECG signal. A problem with such filters is that their increased complexity leads to increased size and cost of the filter. Another problem with such filters is that they typically have increased power consumption compared to simpler filters. These problems with such filters are to be avoided if possible As stated above, filters, such as single pole filters, have been implemented as analog or digital filters. In an attempt to reduce the complexity and resulting costs of filters, particularly baseline wander filters, and also in an attempt to increase the filtering capabilities to more closely approximate the ideal desired filter, digital filtering systems have become the preferred mode of filtering for most signal processing applications such as ECG signal applications. Digital systems allow innovative filter designs to be used based on mathematical techniques. Mathematical filtering techniques are ideally suited to be implemented on a digital system.

One approach to creating these digital filtering systems could be to transform the input ECG signals into a Fourier series corresponding to the input signal. As stated above, a series of sinusoidally varying signals will result at various frequencies with each sine wave having various amplitudes and phases. In the digital filter to remove the baseline wander, the components of the Fourier series having frequencies equal to or higher than the heart beat frequency are passed through the filter. The Fourier series components with slowly varying frequencies, such as those produced by the baseline wander, are removed. In such a filter, it would be highly desirable to build a high pass digital filter with a cutoff frequency of 0.5 Hertz which has a roughly constant delay for all frequencies passed through the filter. A problem with such Fourier transform filters is that it is difficult to perform the required mathematical calculations in real time.

Another approach to providing a digital filter to filter baseline wander has been to use finite impulse response (FIR) filters to filter baseline ECG signals. In the FIR filters, the influence of an input signal on the output of the filter has a finite lifetime, hence the name. Typically, the input ECG signal is sequentially delayed by a series of unit delays. After each delay, the delayed signal is multiplied by a coefficient corresponding to the unit delay. The resulting values from each multiplication operation ar added together to produce the FIR filter output.

The problem with using FIR filters as baseline filters is that they require large numbers of computations to implement the filter. The reasons for the large number of computations is that the number of coefficients required to implement the FIR filter is approximately equal to the inverse of the cutoff frequency of the filter multiplied by the sample rate of the data points presented to the filter. In a typical ECG system, the sample rate is 500 samples per second and the desired cutoff frequency is 0.5 Hz. The number of coefficients needed to implement the corresponding FIR filter would be approximately 1000 coefficients. For each of the 1000 coefficients, there would be a corresponding unit delay so 1000 unit delays would be required to implement the filter. In operation, every part of the ECG signal delayed by the 1000 unit delays would have to be multiplied by its corresponding coefficient and then the resulting values would have to be added together for each sample cycle to produce the output of the FIR filter. If the baseline filtering is to take place in real time using an FIR filter, the filter must be implemented on a powerful computing system. Such systems are typically complex and comparatively expensive.

SUMMARY OF THE INVENTION

A linear phase high pass filter is disclosed using a linear phase low pass filter in parallel with a delay for removing baseline wander from an ECG signal. A digital Infinite Impulse Response (IIR) filter is preferably used as the linear phase low pass filter. An input ECG signal is simultaneously presented to an IIR low pass filter and an electronic delay. Thereafter, the outputs from the IIR low pass filter and delay are passed to a summer where the output from the low pass filter is subtracted from the output of the delay to produce the output of the filter.

The combination of a low pass filter being subtracted from a delayed input signal produces a high pass filter. The resulting high pass filter has a relatively high $-3$ dB cutoff frequency of about 0.5 Hertz while providing a virtually constant group delay for the ECG signal passed through the filter. In this way, distortion of the input ECG signal by the filter is minimized so that the baseline wander portion of the input ECG signals is removed while the part of the input ECG signal representative of the heart function is preserved.

The high pass filter is preferably implemented on a microprocessor which may be part of an ECG processing system. The ECG system may also perform such functions as filtering muscle artifact signals or supplying sample points to a video display system, or both.

It is therefore an object of the instant invention to provide a baseline wander filter which effectively filters baseline wander at all frequencies where it is typically produced while simultaneously providing a virtually constant group delay for all frequencies of ECG signal passed through the filter.

It is a further object of the instant invention to provide a high pass baseline wander filter which may be digitally implemented.

It is a further object of the instant invention to provide a high pass baseline wander filter which is relatively inexpensive and easy to implement.

It is another object of the instant invention to provide a digital high pass baseline wander filter which does not require excessive computations.

It is another object of the instant invention to provide a high pass baseline wander filter which operates in real time.

It is yet another object of the instant invention to provide a high pass baseline wander filter which may produce a desired gain.

It is a further object of the instant invention to provide a high pass baseline wander filter which is comparatively simple to manufacture and operate.

These and other objects of the instant invention will become clear from the description contained herein and more particularly with reference to the following detailed description where like elements are referred to by like reference numbers.

BRIEF DESCRIPTION OF THE DRAWINGS

FIG. 15B is a graph showing the phase shift versus frequency for the high pass baseline filter of FIG. 15A.

DETAILED DESCRIPTION OF THE INVENTION

Figure 5:
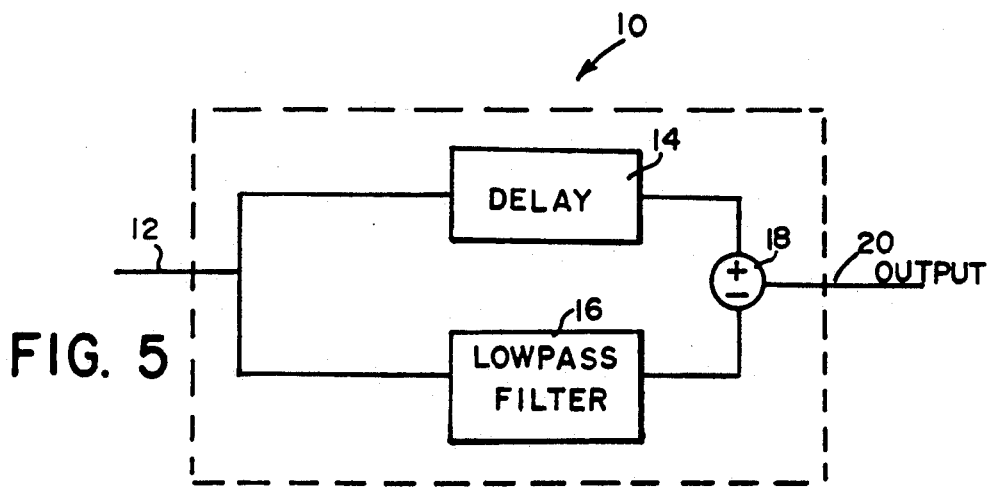
FIG. 5 is a block diagram of the invention.
Figure 3A:
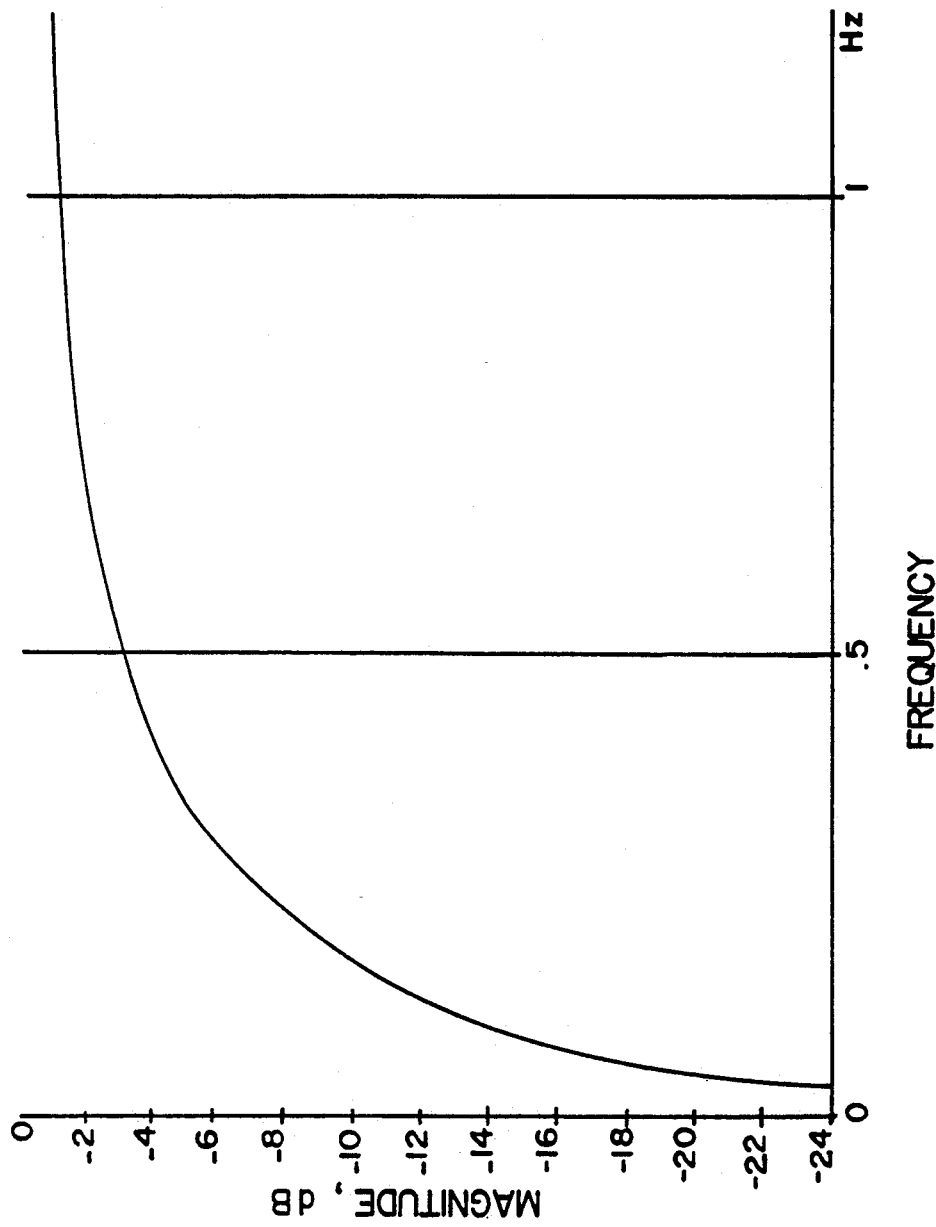
FIG. 3A is a graph representing the magnitude versus frequency for a single pole high pass filter with a −3 dB cutoff frequency of 0.5 Hz.
Figure 3B:
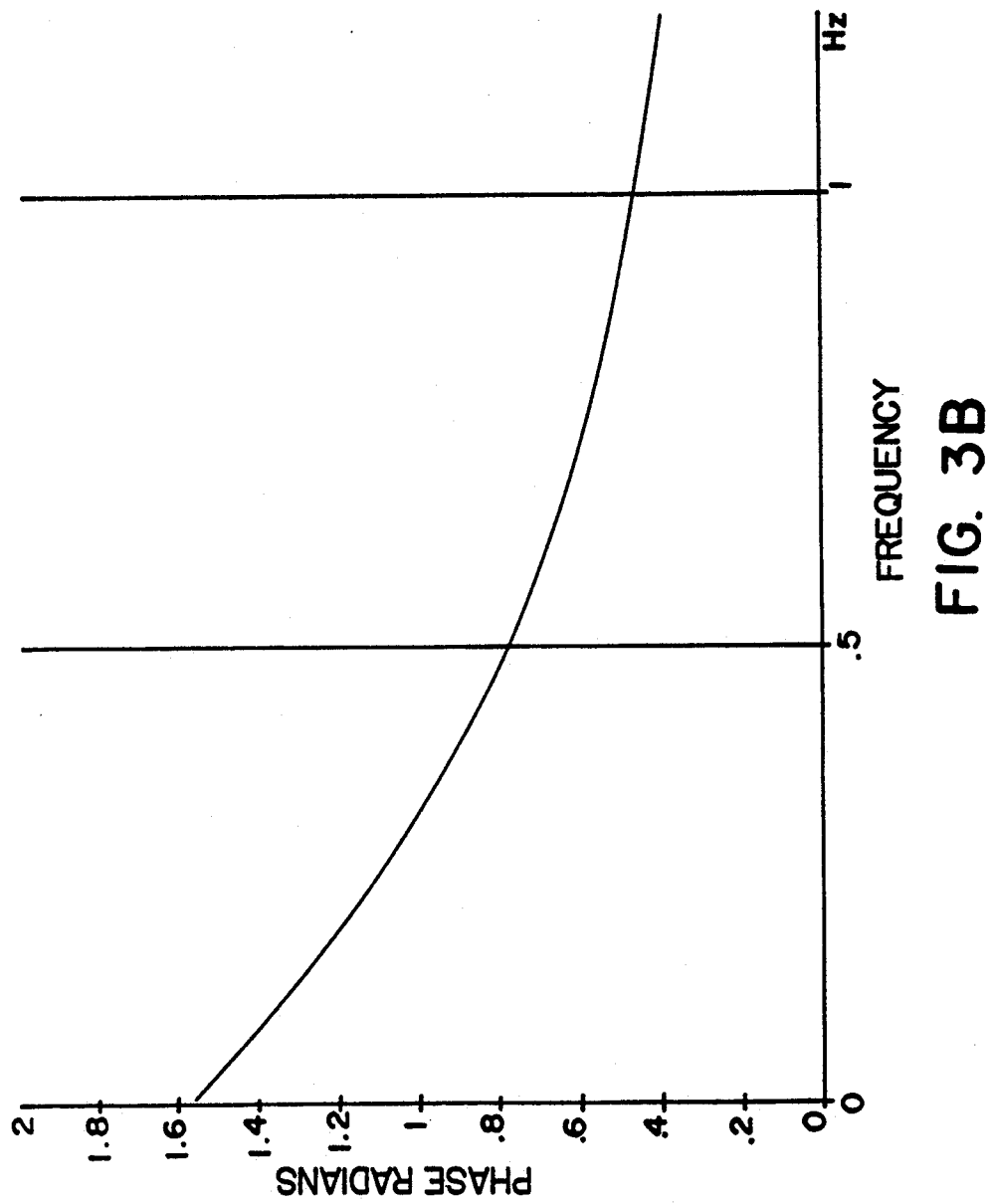
FIG. 3B is a graph showing the phase shift verses frequency for the filter of FIG. 3A.
Figure 3C:
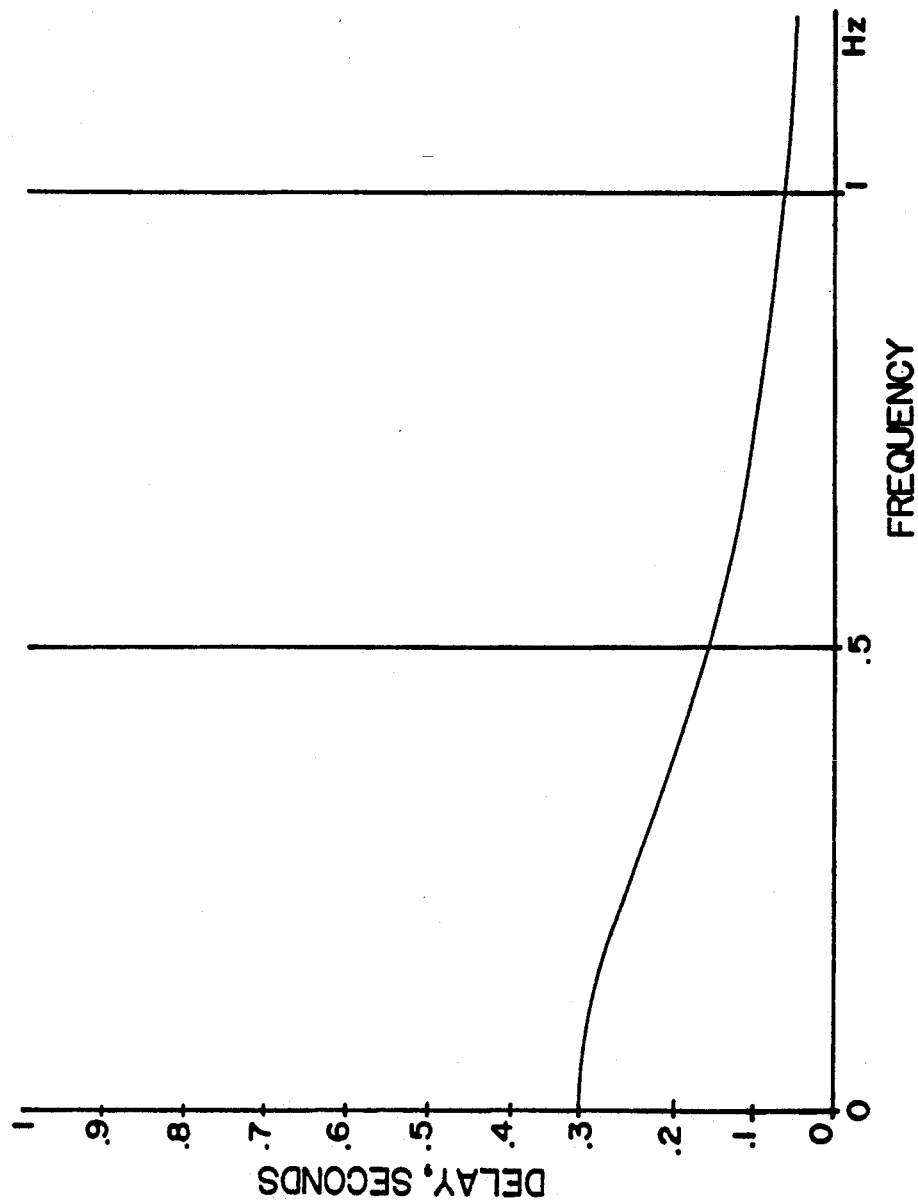
FIG. 3C is a graph showing the delay versus frequency for the filter of FIG. 3A.
Figure 4A:
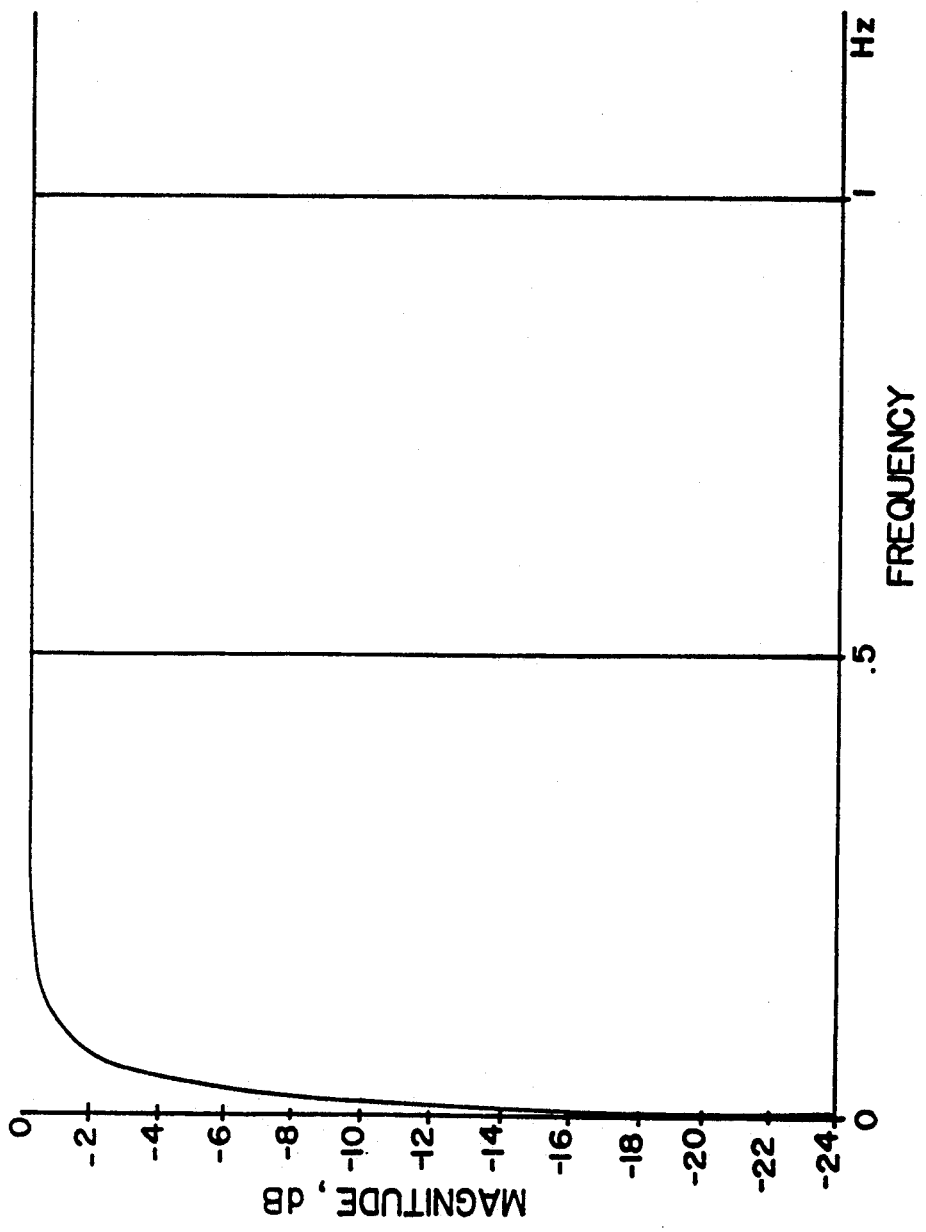
FIG. 4A is a graph showing the magnitude versus frequency for a single pole high pass filter having a −3 dB cutoff frequency of 0.05 Hz.
Figure 4B:
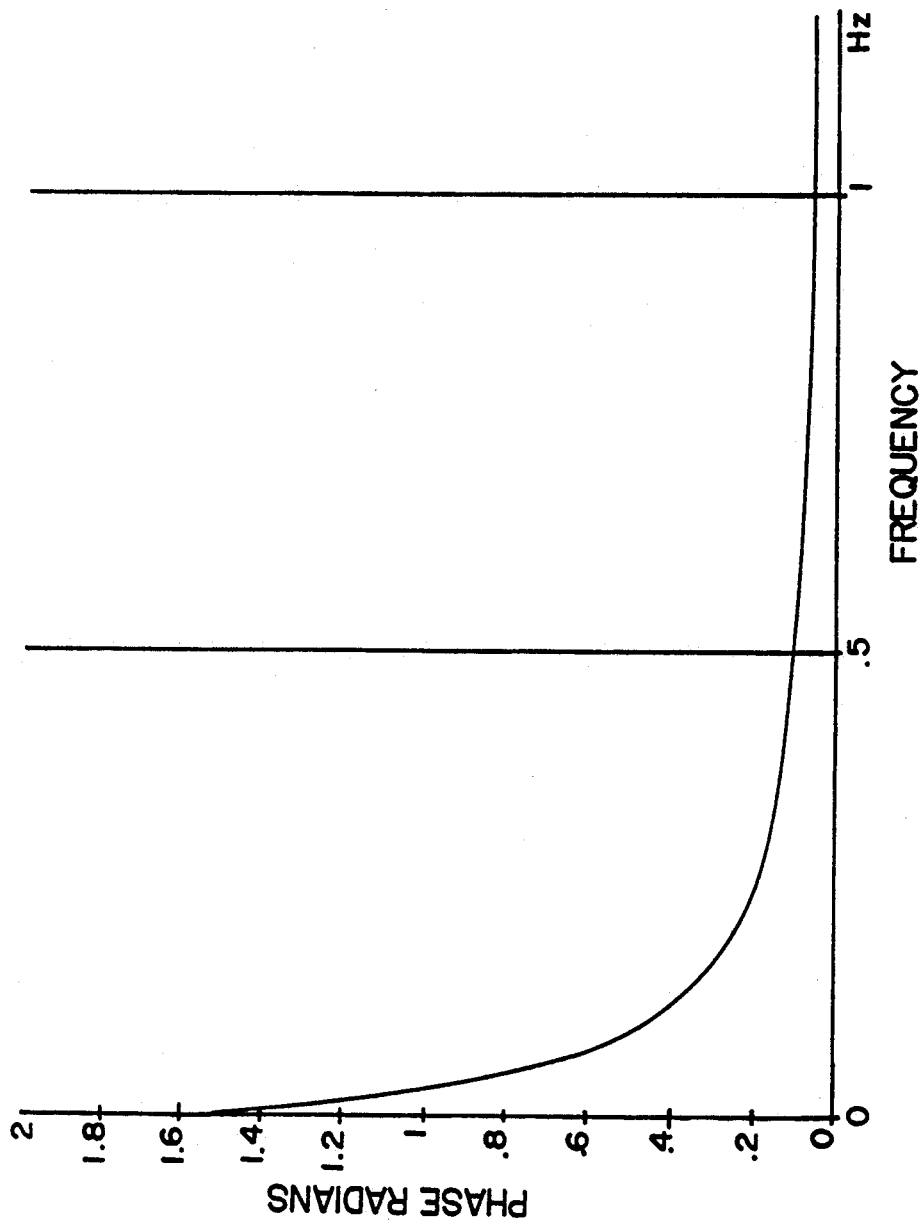
FIG. 4B is a graph showing the phase shift versus frequency for the filter of FIG. 4A.
Figure 4C:
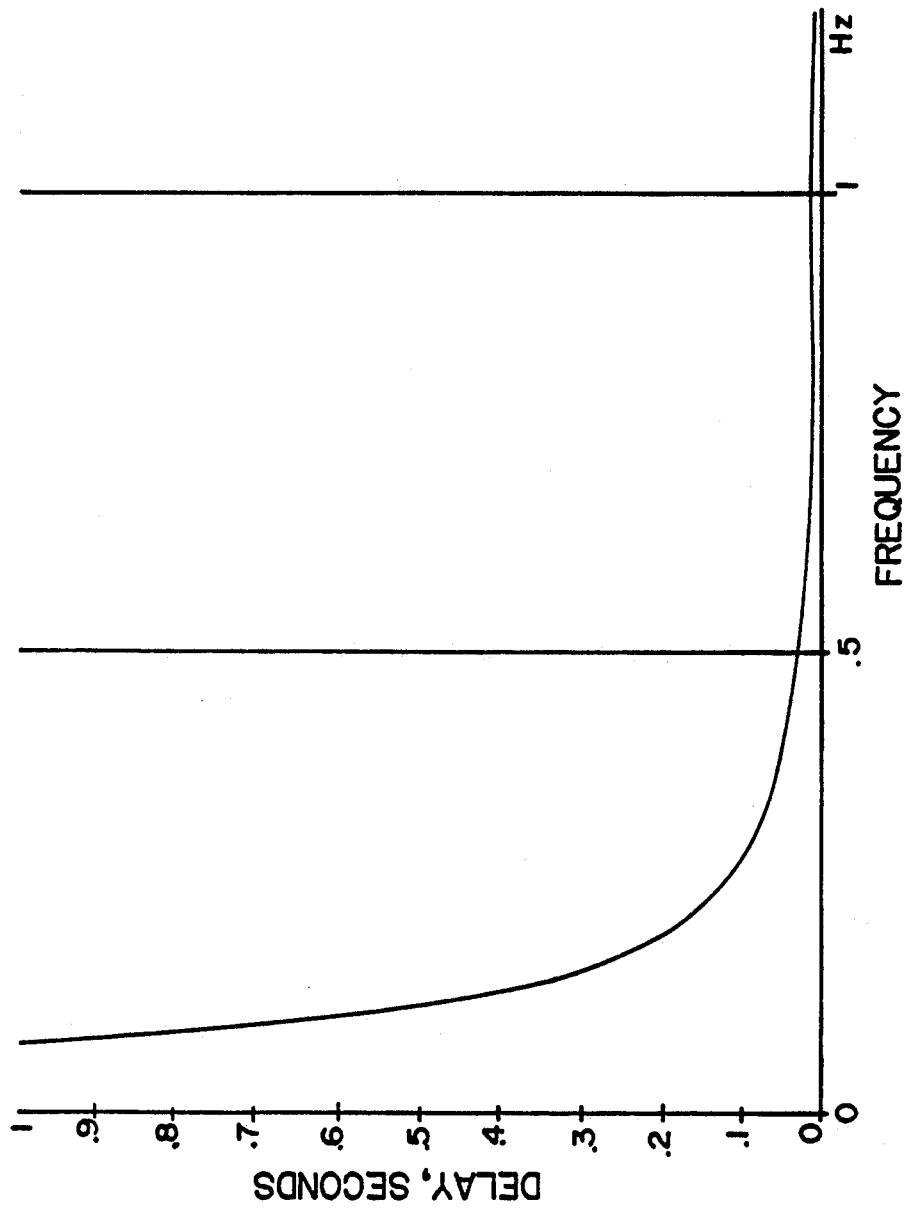
FIG. 4C is a graph showing the delay versus frequency for the filter of FIG. 4A.

The instant invention is shown generally labeled 10 in the block diagram of FIG. 5. An input ECG signal is presented to the filter input 12 where it is split and simultaneously presented to an electronic delay 14 and a linear phase low pass filter 16. Delay 14 electronically delays the ECG signal input at input 12 for a time equal to the processing time of low pass filter 16 by techniques which are well known in the art. Delay 14 is preferably a digital delay such as is common in the art whereby input digital signals are electronically delayed for a prespecified number of unit delay periods. Typically, such delays 14 include electronic memory which stores sequential portions of the input signal for the desired time delay. The outputs from both delay 14 and low pass filter 16 are presented to summer 18.

Delay 14 provides an electronic delay of the input ECG signal for the time it takes low pass filter 16 to perform its low pass filtering function. This allows the identical part of the ECG signal passed through both delay 14 and low pass filter 16 to be presented to summer 18 at the same time. The workings of summer 18, as well as summers 24, 32, 46, 64, and 76 described hereafter, are well known in the art. Summers are sometimes represented schematically by the symbol "Σ". At summer 18, the output of low pass filter 16 is subtracted from the output of delay 14. By subtracting the ECG signal processed by low pass filter 16 from the delayed input ECG signal passed through delay 14, an effective high pass filter is created. The output of summer 18 is presented to output 20 so that the signal output from output 20 is the high pass filter output of the filter 10.

The input ECG signal presented to filter input 12 has two parts superimposed on each other: a signal part generated by the heart; and, a signal part not generated by the heart. The purpose of the instant invention 10 is to remove the signal part of the input ECG signal not generated by the heart from the input ECG signal thereby leaving the signal part of the input ECG signal generated by the heart.

In particular, the signal part of the input ECG signal not generated by the heart comprising a slowly varying voltage known as baseline wander is to be removed from the input ECG signal. In this regard, the function of low pass filter 16 is to remove the part of the input ECG signal generated by the heart from the input ECG signal thereby leaving the part of the input ECG signal not generated by the heart which remaining signal part is manifest as baseline wander. Low pass filter 16 passes this very low frequency baseline wander signal while attenuating the higher frequencies of the heart generated part of the input ECG signal. Therefore, the output of low pass filter 16 is essentially the baseline wander signal which has been removed from the input ECG signal. This baseline wander signal output for low pass filter 16 is removed from the input ECG signal at summer 18 by subtracting the baseline wander signal from the input ECG signal, which includes the baseline wander signal, which input ECG signal has been delayed by delay 14. The resulting signal output from high pass filter 10 is a filtered ECG signal containing only the part of the input ECG signal produced by the heart.

Linear phase low pass filter 16 is preferably a digital Infinite Impulse Response (IIR) filter. The schematic of one embodiment of the linear phase low pass filter 16 is shown in detail in FIG. 6. The high pass filter 10 implementing this embodiment of filter 16 is preferably used to filter baseline wander from the ECG signal before the filtered signal is passed to diagnostic circuitry but may be used in other applications as well, such as filtering the ECG signal before passing it to a device to visually display the ECG signal. As can be seen with reference to FIG. 6, the linear phase low pass filter 16 of this embodiment is a fifth order three stage filter. Although this embodiment of filter 16 is a fifth order filter, other filters of higher or lower order, particularly a third order filter, as will be described hereafter, may be used in certain applications as desired. As is well known in the art, the higher the order of the filter, the sharper the cutoff at the cutoff frequency of the filter. A sharp cutoff is generally a desirable feature of a filter. An additional benefit of using higher order filters is that there is better phase linearity near the cutoff frequency and throughout the frequency spectrum passed through the filter. This phase linearity manifests itself in lower distortion of the signal passed through the filter and in a near constant delay of the signal by the filter regardless of the frequency of the signals passed through the filter 16.

However, although the delay of the signal through the filter is near constant for higher order filters, the delay is greater for higher order filters than it is for lower order filters. A consequence of using a higher order filter with its greater delay is that the memory size of delay 14 must be increased in order to accommodate the larger amount of data required to be stored in delay 14 in order to produce a delay matching in time the delay of the filter 16. This larger memory size of delay 14 leads to increased costs.

An additional problem of using higher order filters with their corresponding relatively greater delays is that the increased delay of the ECG signal passing through the filter 16 causes an increased delay between what the heart is currently doing and the manifestation of the ECG signal on a video display screen or a chart recorder. In the instant invention, the delay for the fifth order filter 16 has been found to be about one and a half seconds, while the delay for a third order filter 16, described hereafter and made according to the instant invention, has been found to be about 0.8 seconds.

For many applications it is desirable to have a short delay between the collection of the electrical potentials of the heart and their display. As a result, in one embodiment of the invention described hereafter, the high pass filter 10 uses a third order filter for low pass filter 16. This embodiment of high pass filter 10 is used to filter baseline wander from the ECG signal before displaying the ECG signal on a video display screen or a chart recorder in order to provide the doctor with a relatively current ECG display. However, the fifth order filter 16 is preferably used in the embodiment of high pass filter 10 used to filter the baseline wander from the ECG before passing the filtered ECG signal to diagnostic circuitry since the distortion of the ECG signal by the fifth order filter due to non-linearity of the phase shift of the filter 16 is less than the similar distortion produced by the third order filter. The third order filter, although producing more distortion of the ECG signal as a result of the filtering process than the fifth order filter, produces an adequate filtering result for visual diagnosis of the ECG signal. However, the fifth order filter produces the better filter results required by the more sophisticated electronic analysis circuitry commonly used in ECG diagnostic systems.

Figures 6, 7, 8:
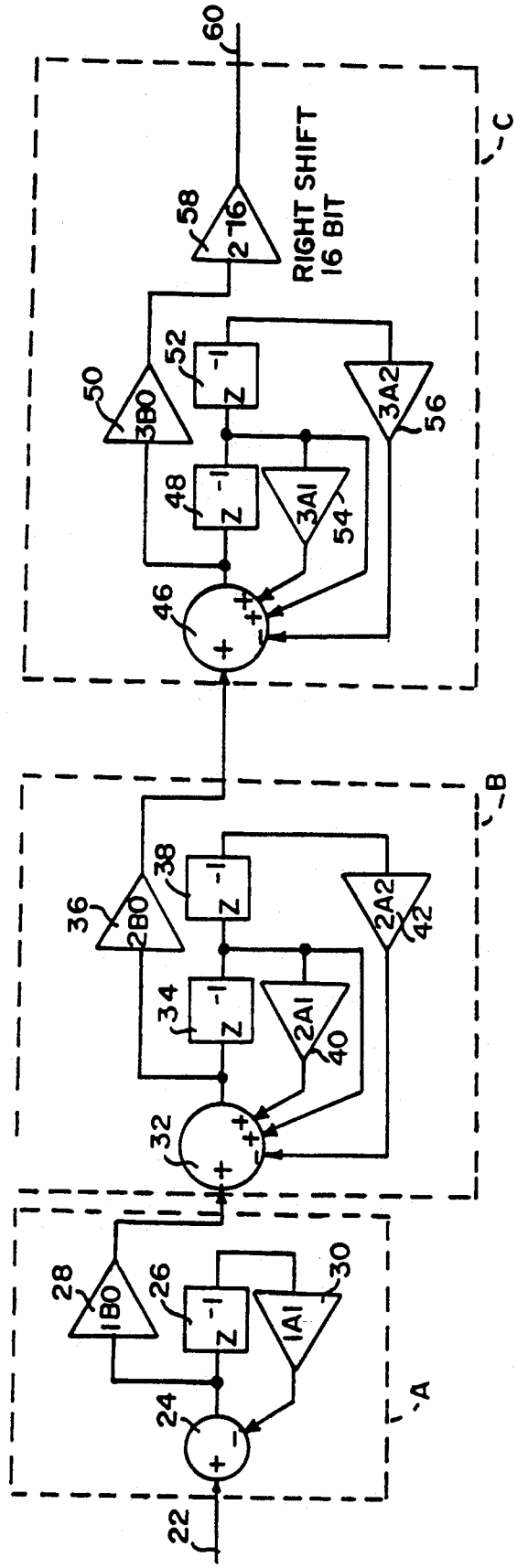
FIG. 6 is a schematic diagram of one embodiment of the IIR low pass filter of the instant invention.
FIG. 7 is a table showing the coefficients for the filter of FIG. 6.
FIG. 8 is a table showing the gains for the three stages of the filter of FIG. 6.

The three stages of the fifth order embodiment of filter 16 shown in FIG. 6, have been outlined in dotted lines in FIG. 6 and designated with the letters A, B and C. Stage A is a first order stage because it contains one unit delay labeled 26. Stages B and C are second order stages since they each contain two unit delays labeled 34,38 and 48,52 respectively.

In FIG. 6, the first order stage A is placed along the filtering path before second order stages B and C in order to produce an output signal from stage A of appropriate gain to prevent the subsequent stages B and C from being overwhelmed by a high amplitude input ECG signal. The stages A, B and C of the filter 16 amplify the frequency components of the input ECG signal by varying amounts depending on the frequency of the components of the ECG signal. Typically, first order stages amplify all frequency components less than second order stages. In the instant invention, the first order stage A has been designed to attenuate frequency components of the ECG signal which would cause problems in the subsequent second order stages B and C. The particular problem that occurs in second order stages such as B and C that stage A minimizes is that at specific frequencies, the second order stages have a very high gain which overwhelms the arithmetic computation ability of the system.

For example, in one embodiment of the instant invention, a microprocessor is used to implement 48 bit 2's complement arithmetic where 32 bits are used to represent the integer values of the ECG signal and the remaining 16 bits are used to represent the fractional values of the ECG signal. When using the coefficients shown in FIG. 7, the gains for the corresponding stages A, B and C are shown in FIG. 8. As can be seen, the gain for stage A is about 51 while the gains for stages B and C are about 356 and 964 respectively. The largest input value preferably presented to the input 22 of the low pass filter 16 is the binary equivalent of the decimal number 2047 which in binary is 11 "ones". If this maximum input signal were passed through the entire filter without attenuation, the resulting gain expressed as a decimal number would be nearly 36 billion. However, the 32 integer bits of the 48 bit data can only hold a binary number whose decimal equivalent is about 2.1 billion. Consequently, without providing some means to keep the data smaller than maximum value allowed by the microprocessor, an input ECG signal of maximum permissible amplitude would overwhelm the microprocessor. As a result, stages A and B have gain blocks 28 and 36 respectively and stage C has gain blocks 50 and 58 which attenuate the output from each stage A, B and C, respectively, before passing the output of the stage to the next stage, or the ultimate output of low pass filter 16 in the case of stage C.

The gain blocks 28, 36 and 50 have corresponding coefficients $1B_0$, $2B_0$ and $3B_0$ respectively. The coefficient values for the fifth order, three stage embodiment of the invention shown in FIG. 6 are shown in FIG. 7.

Although the embodiment of the fifth order, three stage filter described herein has the first order stage A preceding the two second order stages B and C, it is not necessary that the stages be arranged in this order. In fact, these stages may be arranged in any order, as desired, and will still produce the same filtering results described herein. However, if other arrangements of the stages are used, care must be taken to ensure that the gains of the various stages do not produce signal levels which overwhelm the computational ability of the microprocessor doing the calculations.

Referring to FIG. 6, the input ECG signal from input 12 is presented to filter input 22 which is immediately passed to summer 24. At summer 24, the ECG signal input at filter input 22 has the output of multiplication block 30 subtracted from it as will be described hereafter. The output of summer 24 is simultaneously presented to delay 26 and to gain block 28.

Delay 26, as does delays 34, 38, 48, and 52, provides a unit delay for the signal presented to their respective inputs. In this case, delay 26 provides a unit delay for the output of summer 24. After the output of summer 24 is delayed by delay 26, the signal passes to multiplication block 30 where the signal is multiplied by the coefficient represented by $1A_1$. The value of coefficient $1A_1$ is found in the table shown in FIG. 7 along with the other coefficients used in the embodiment shown in FIG. 6. The coefficients shown in FIG. 7 are chosen to produce a low pass filter 16 having a $-3$ dB cutoff frequency of 0.2789 Hz and an output gain at D.C. of 1. It will be clear to those skilled in the art that the coefficient values contained in FIG. 7 may be varied to produce different output gains while maintaining the same $-3$ dB cutoff frequency. Further, the coefficients of FIG. 7 may be modified to produce other cutoff frequencies as desired. Of course, the coefficients of FIG. 7 may also be modified so that both the cutoff frequency and the gain may be modified as desired.

The output of multiplication block 30 is presented to summer 24 where it is subtracted from the input ECG signal presented at filter input 22. Of course, the signal output from multiplication block 30 and presented to summer 24 has been delayed so that when it is subtracted from the ECG signal at summer 24, the ECG signal at filter input 22 is a part of the ECG signal later in time than the part of the ECG signal which has produced the output of multiplication block 30.

It is important to note that the output of summer 24 contains a new part and an old part. The new part is the addition of the current ECG signal presented to filter input 22. The old part is the output of multiplication block 30 which is subtracted from the input ECG signal presented at filter input 22. But, after the input ECG signal has been added to the output of multiplication block 30, the resulting output of summer 24 is passed through delay 26 and multiplication block 30 back to be subtracted from the input ECG signal at summer 24. In this way, the input ECG signal has a continuing existence as it is cycled through the loop from summer 24 through delay 26 and multiplication block 30 back to summer 24. It is because of the continuous existence of the influence of the input ECG signal that this type of filter is called an "Infinite Impulse Response" (IIR) filter. As mentioned, the output of summer 24 is also presented to gain block 28. Gain block 28 multiplies the output of summer 24 by the coefficient designated $1B_0$. The output of gain block 28 is the output of stage A. In the embodiment shown in FIG. 6 using the coefficients of FIG. 7, the value of coefficient $1B_0$ is 1. In this case gain block 28 could be eliminated. However, if it is desired to produce an overall gain for the filter 16 different from the gain of about 1 produced by the coefficients in FIG. 7 as discussed above, the coefficient $1B_0$ of gain block 28 could be changed to a value different than 1.

The output of gain block 28 is presented to the input of stage B at summer 32 where the output of stage A is added to the outputs of various elements of stage B. The output of summer 32 is simultaneously presented to unit delay 34 and gain block 36. Unit delay 34 delays the output signal from summer 32 by a unit time period. The output of unit delay 34 is simultaneously presented three different places: unit delay 38; multiplication block 40; and, summer 32. Delay 38 delays the output signal from delay 34 by a unit time period whereafter the output of unit delay 38 is presented to multiplication block 42. Multiplication block 42 multiplies the output signal of delay 38 by the coefficient $2A_2$. The output of multiplication block 42 is presented to summer 32 where it is subtracted from the output of stage A.

As stated, the output of delay 34 is presented to multiplication block 40. Multiplication block 40 multiplies the output signal of delay 34 by the coefficient $2A_1$. Thereafter, the output of multiplication block 40 is presented to summer 32 where it is added to the signal output from stage A.

The output of summer 32 is also presented to gain block 36 which multiplies the output of summer 32 by the coefficient labelled $2B_0$. As explained in detail above, gain block 36 reduces the gain inherent in stage B so that a signal is presented to stage C at a level that won't overwhelm the computational abilities of stage C. The output of gain block 36 is the output of stage B. The output of stage B is presented to stage C at summer 46.

Summer 46 adds the output of stage B to the results of the processing of stage C as will be described hereafter. The output of summer 46 is simultaneously presented to unit delay 48 and gain block 50. The output of unit delay 48 is simultaneously presented to unit delay 52, multiplication block 54, and summer 46. Multiplication block 54 multiplies the output of unit delay 48 by the coefficient labelled $3A_1$, whereafter the output of multiplication block 54 is added to the output of stage B at summer 46.

The output of unit delay 48 is also passed to delay 52 where it is delayed by unit delay 52. The output of unit delay 52 is passed to multiplication block 5 where it is multiplied by the coefficient labelled $3A_2$. Thereafter, the output of multiplication block 56 is presented to summer 46 where it is subtracted from the output of stage B.

As described above, the output of summer 46 is passed to gain block 50 where the signal is multiplied by the coefficient $3B_0$. Thereafter, the output of gain block 50 is passed to gain block 58. Gain block 58, in this embodiment, multiplies the output of gain block 50 by $2^{-16}$. This is accomplished by right shifting the output from gain block 50 by 16 bits. The net effect of multiplying the output of summer 46 by the coefficient $3B_0$ and then by $2^{-16}$ is to multiply the output of summer 46 by about $1.9 \times 10^{-6}$. Of course, gain blocks 50 and 58 could be combined into a single gain block which multiplies the output of summer 46 by about $1.9 \times 10^{-6}$.

The output of gain block 58, in this embodiment, is the baseline wander signal with an amplitude about equal to the amplitude of the baseline wander signal when it was combined with the heart generated ECG signal in the input ECG signal. The effect of multiplying the output of summer 46 by about $1.9 \times 10^{-6}$ is to produce a overall gain of filter 16 at D.C. of about 1 despite the gains of stages A and B and stage C before gain blocks 50 and 58, totalling about 17 million. In other words, the net gain of the filter 16 for the signals passed through the filter 16, which are low frequency signals primarily consisting of the baseline wander signal, using the coefficients in FIG. 7, is about one. The output of gain block 58 is the output 60 of the low pass filter 16. Of course, as stated above, the coefficients of FIG. 7 could be changed to produce other desired gains or cutoff frequencies, or both, if desired.

As stated, the coefficients of the embodiment of the instant invention shown in FIG. 6 necessary to produce a fifth order three stage low pass filter with a cutoff frequency of 0.2789 Hertz and a gain at D.C. of 1 are shown in FIG. 7. As can be seen, all the coefficients have values less than 1 and are positive. Therefore, in this embodiment as implemented on the microprocessor described above, the coefficients are represented in the registers of the microprocessor by 16 bit unsigned numbers.

Figure 12A:
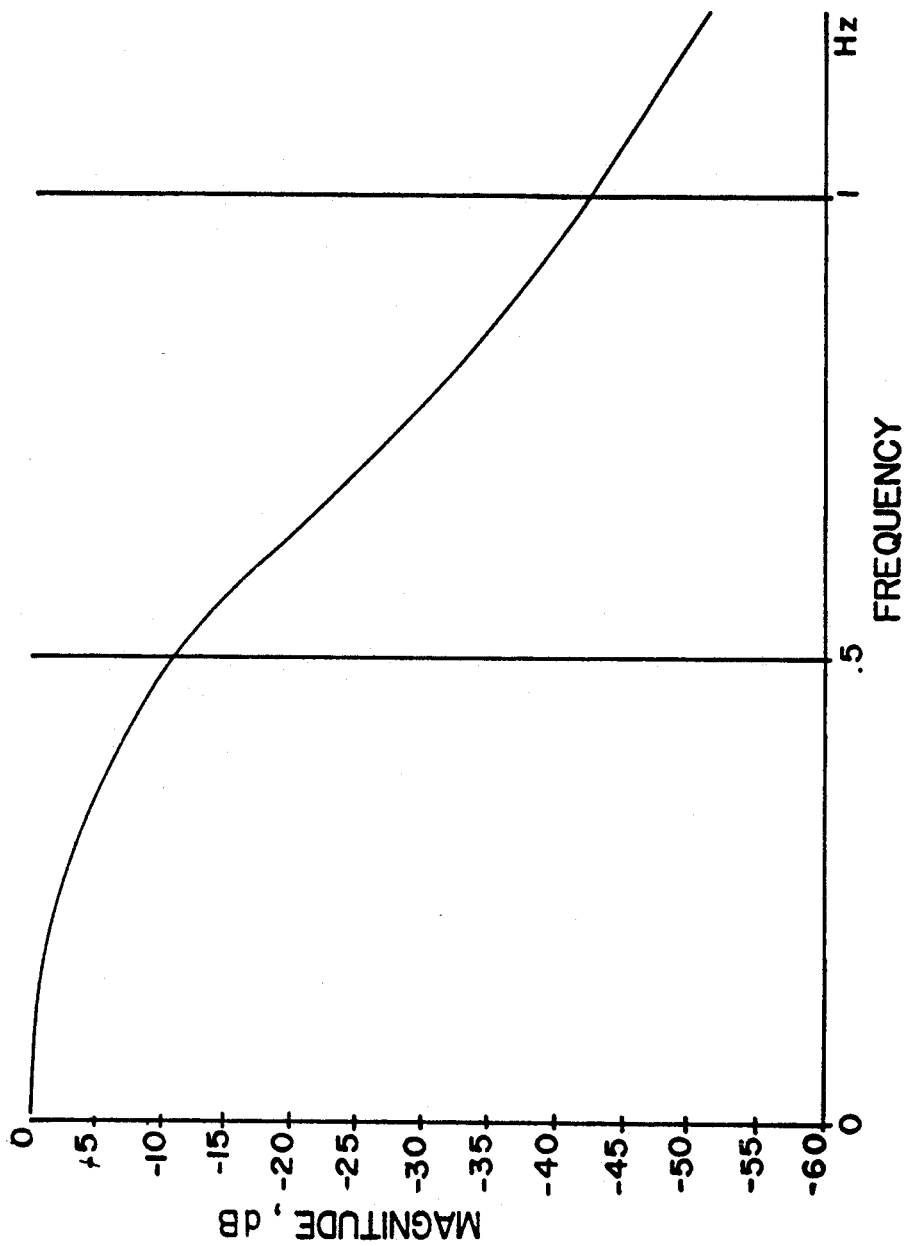
FIG. 12A is a graph showing the magnitude versus frequency for the filter of FIG. 6.
Figure 12B:
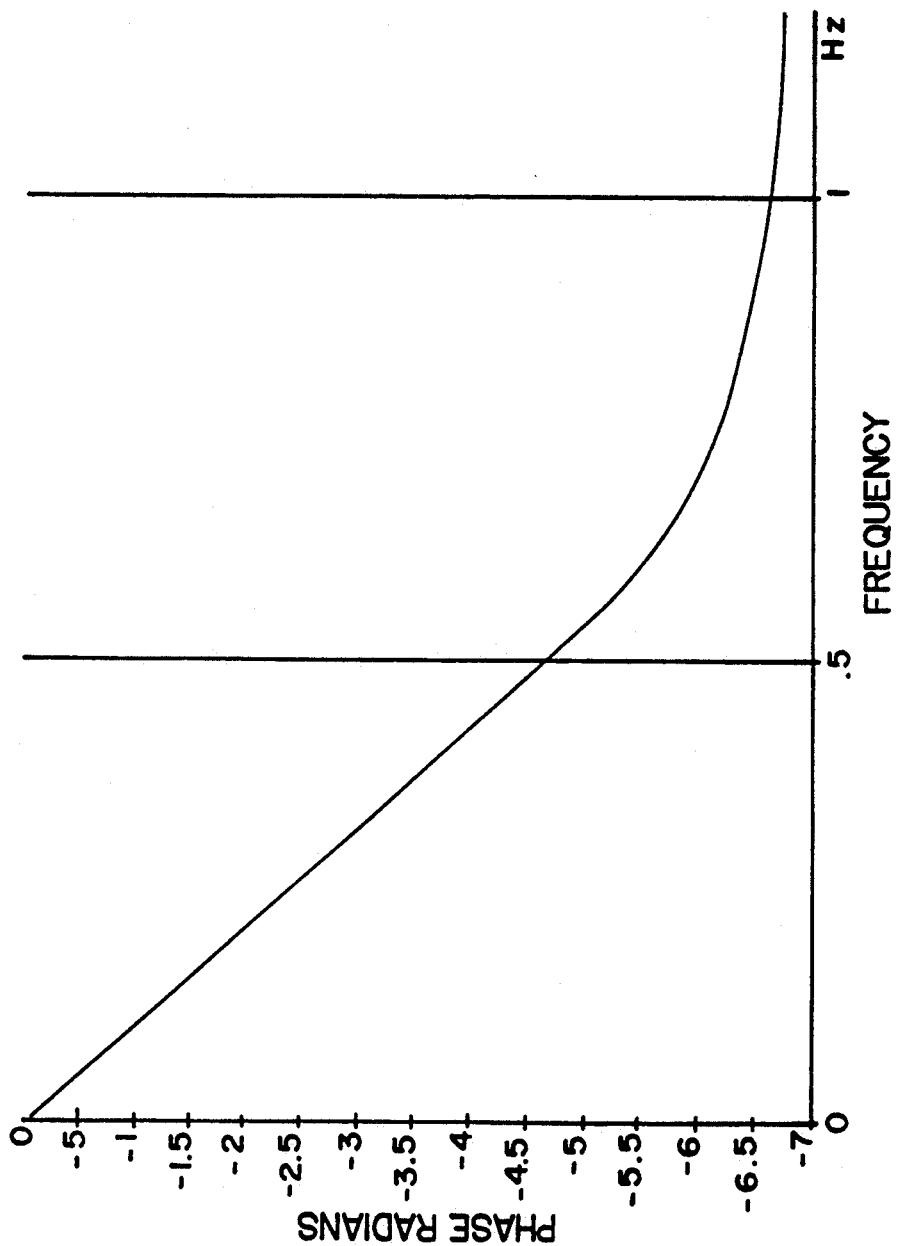
FIG. 12B is a graph showing the phase shift versus frequency for the filter of FIG. 12A.
Figure 12C:
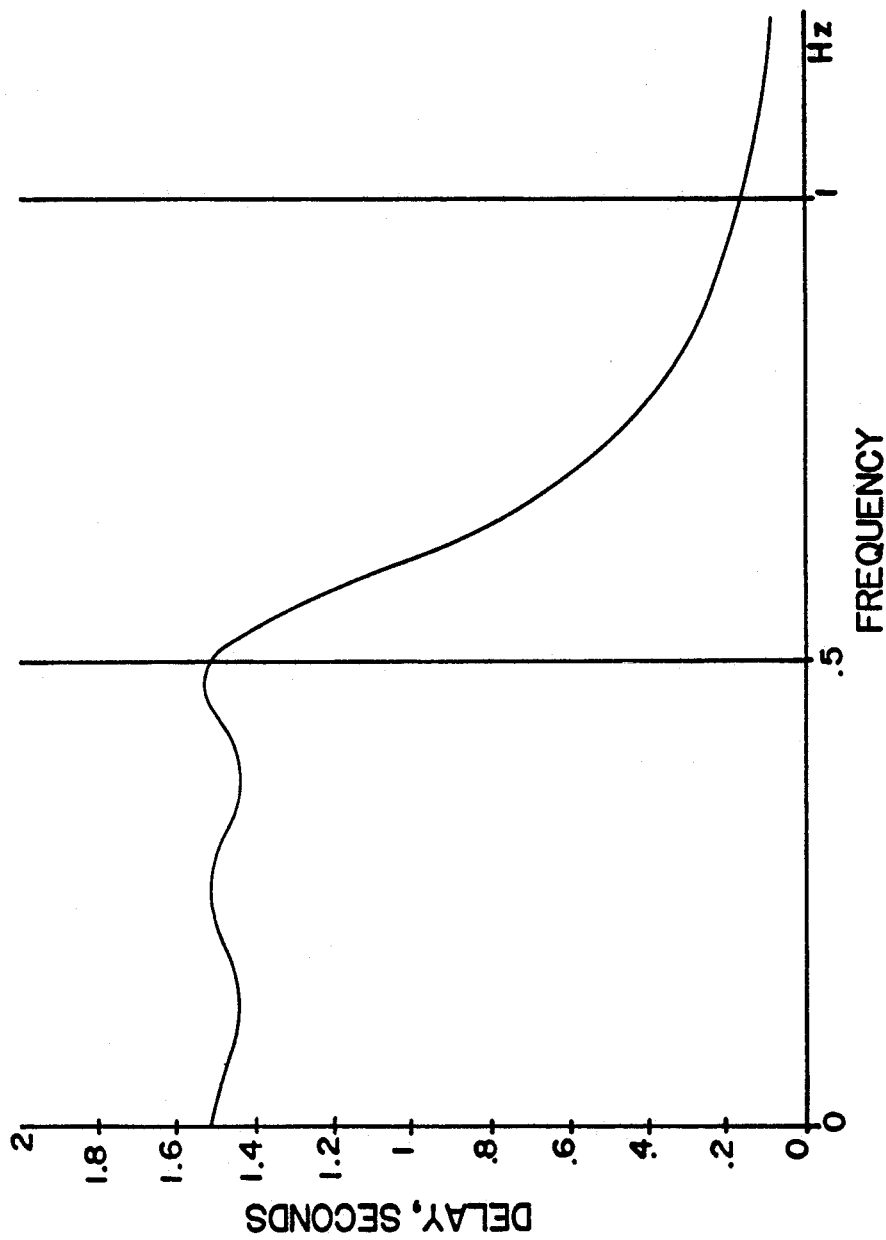
FIG. 12C is a graph showing the delay versus frequency for the filter of FIG. 12A.

A graph showing the amplitude versus frequency of this embodiment of the filter 16 is shown in FIG. 12A. The phase versus the frequency for this embodiment is shown in the graph of FIG. 12B. As can be seen, the phase is linear over the range of 0 Hz to about 0.6 Hz. The corresponding delay of the ECG signal versus frequency is shown in the graph of FIG. 12C. As can be seen, the delay is nearly constant for frequencies below the cutoff frequency of this low pass filter.

Figure 1:
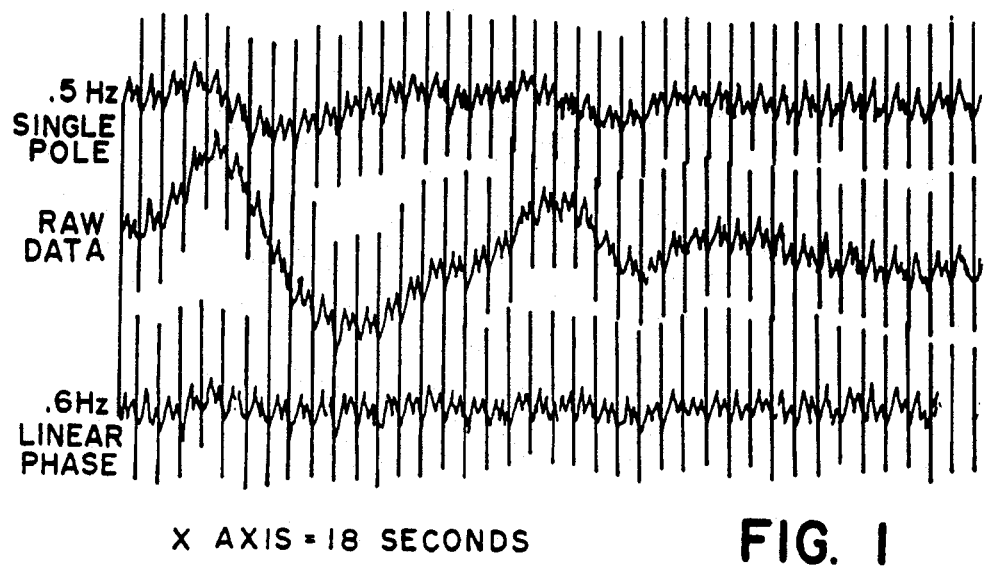
FIG. 1 is a diagram showing an unfiltered ECG trace having baseline wander which unfiltered ECG trace is aligned with both an ECG trace filtered by a 0.5 Hz single pole filter and an ECG trace filtered by a 0.6 Hz linear phase five pole three stage filter made according to the instant invention.
Figure 2:
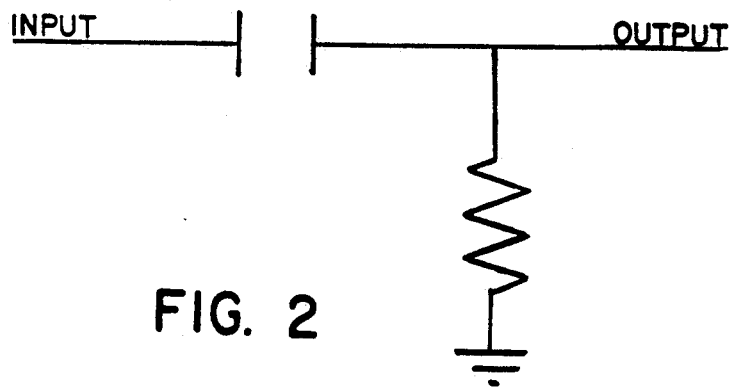
FIG. 2 is a schematic diagram of a single pole filter.
Figure 14A:
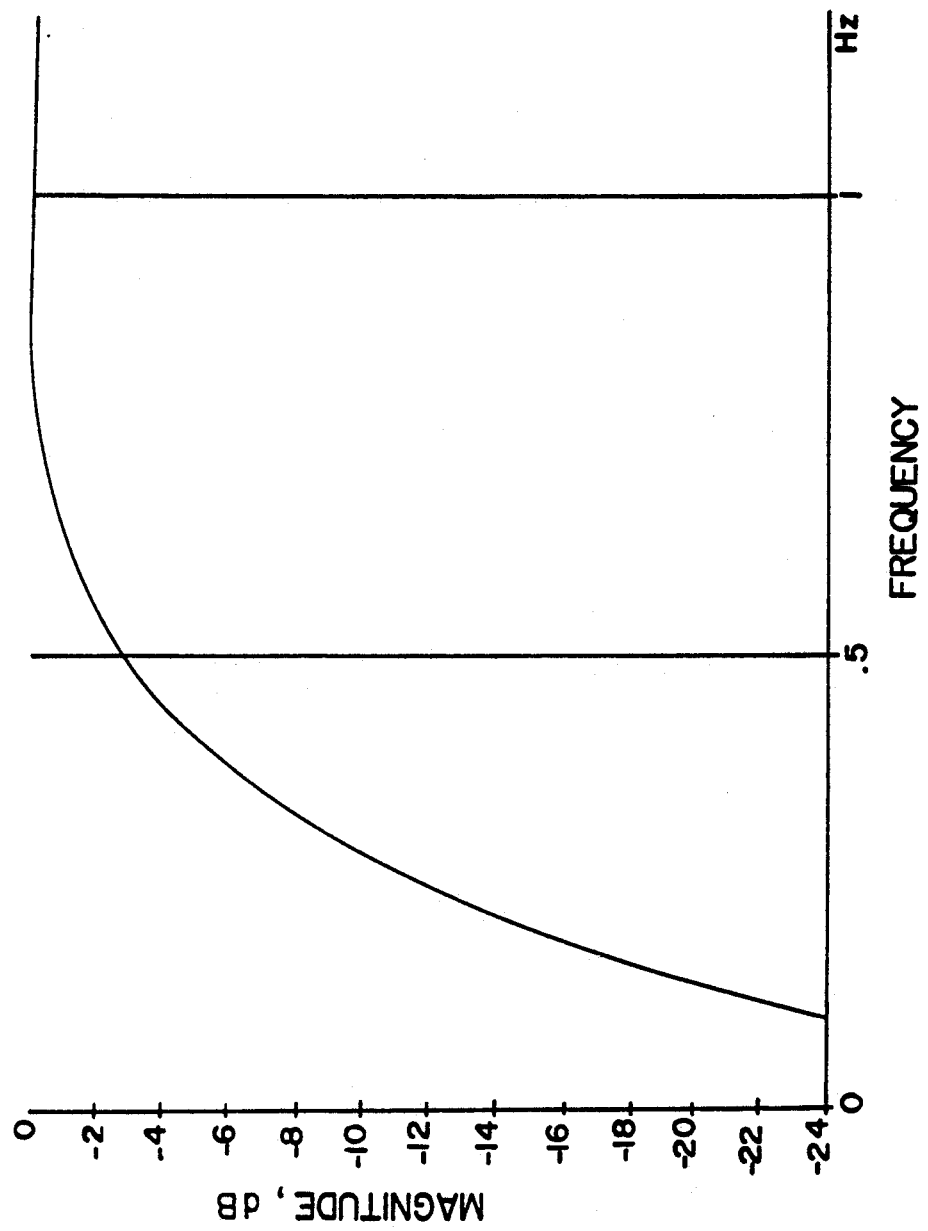
FIG. 14A is a graph showing the magnitude versus frequency for the high pass baseline wander filter of FIG. 5 using the low pass filter of FIG. 6.
Figure 14B:
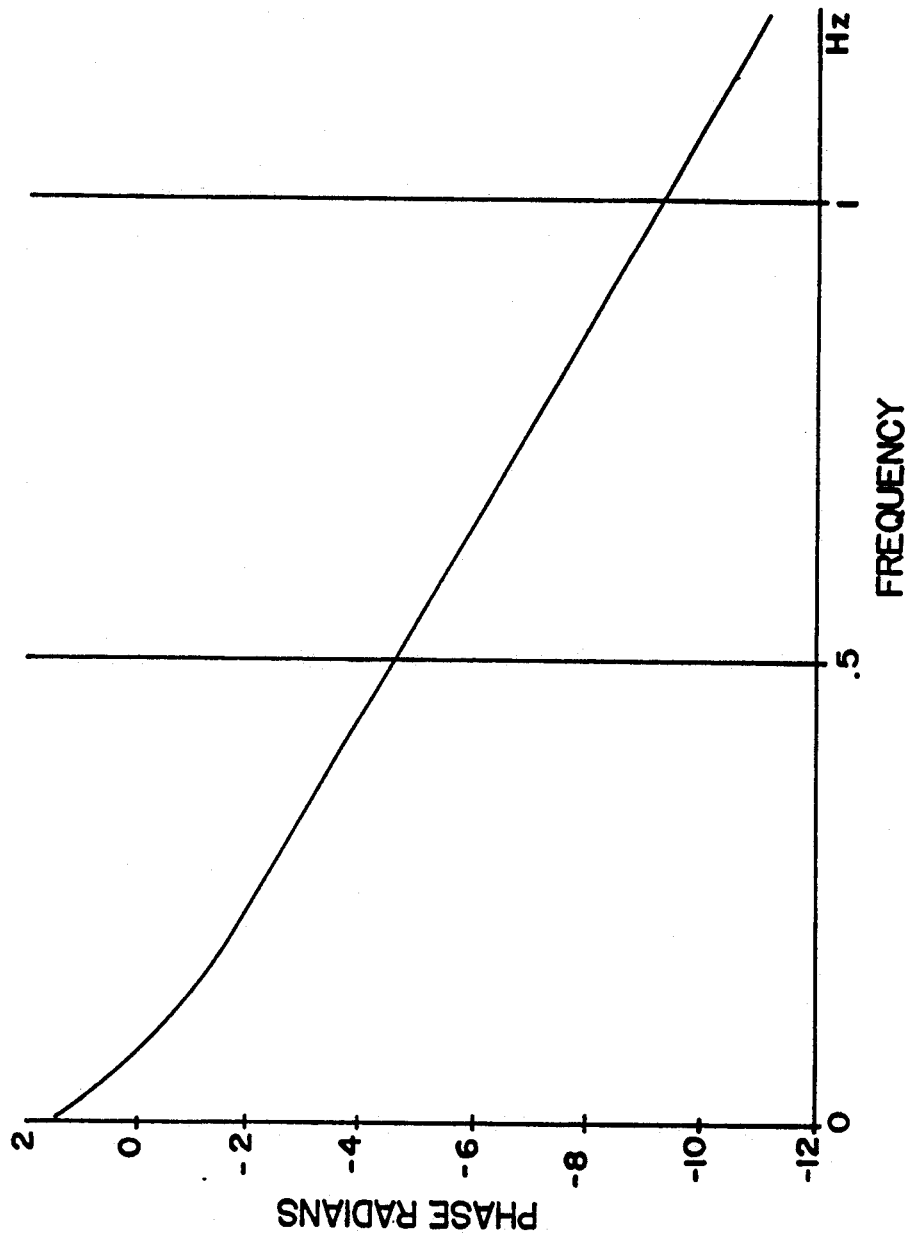
FIG. 14B is a graph showing the phase shift versus frequency for the high pass baseline filter of FIG. 14A.
Figure 14:
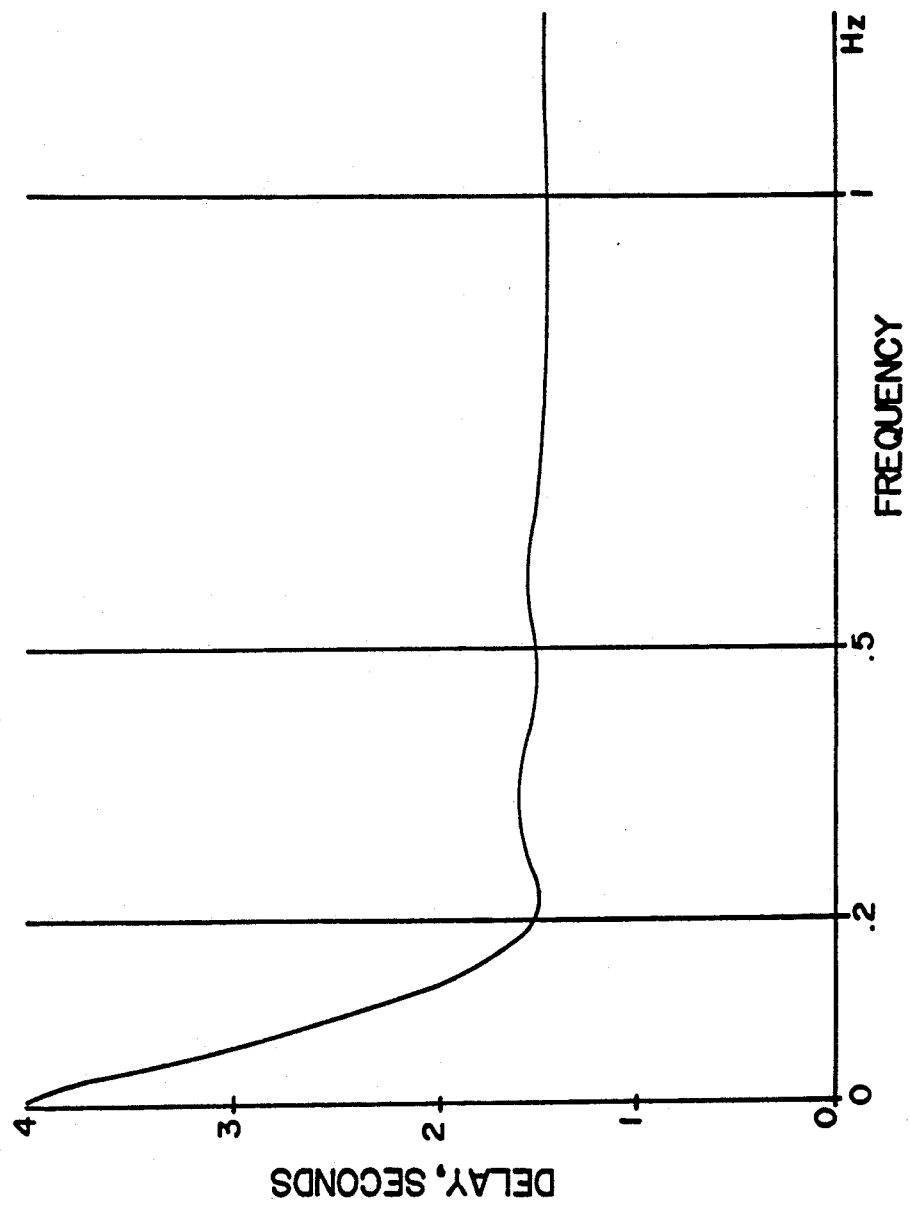
FIG. 14C is a graph showing the delay versus frequency for the high pass baseline filter of FIG. 14A.

The output of low pass filter 16 at output 60 is presented to summer 18 where it is subtracted from the output of delay 14 as explained above. The resulting filter 10 is a high pass filter having a $-3$ dB cutoff frequency of about 0.5 Hz as is shown in FIG. 14A. FIGS. 14B and 14C show the phase shift and delay versus frequency, respectively, for the filter 10 explained above. As can be seen, the phase is linear and the delay constant over the frequencies passed through the filter 10. The output of such a filter 10 is shown in FIG. 1 aligned with the original input ECG signal having baseline wander. As can be seen, the baseline wander is virtually eliminated.

Figures 9, 10, 11:
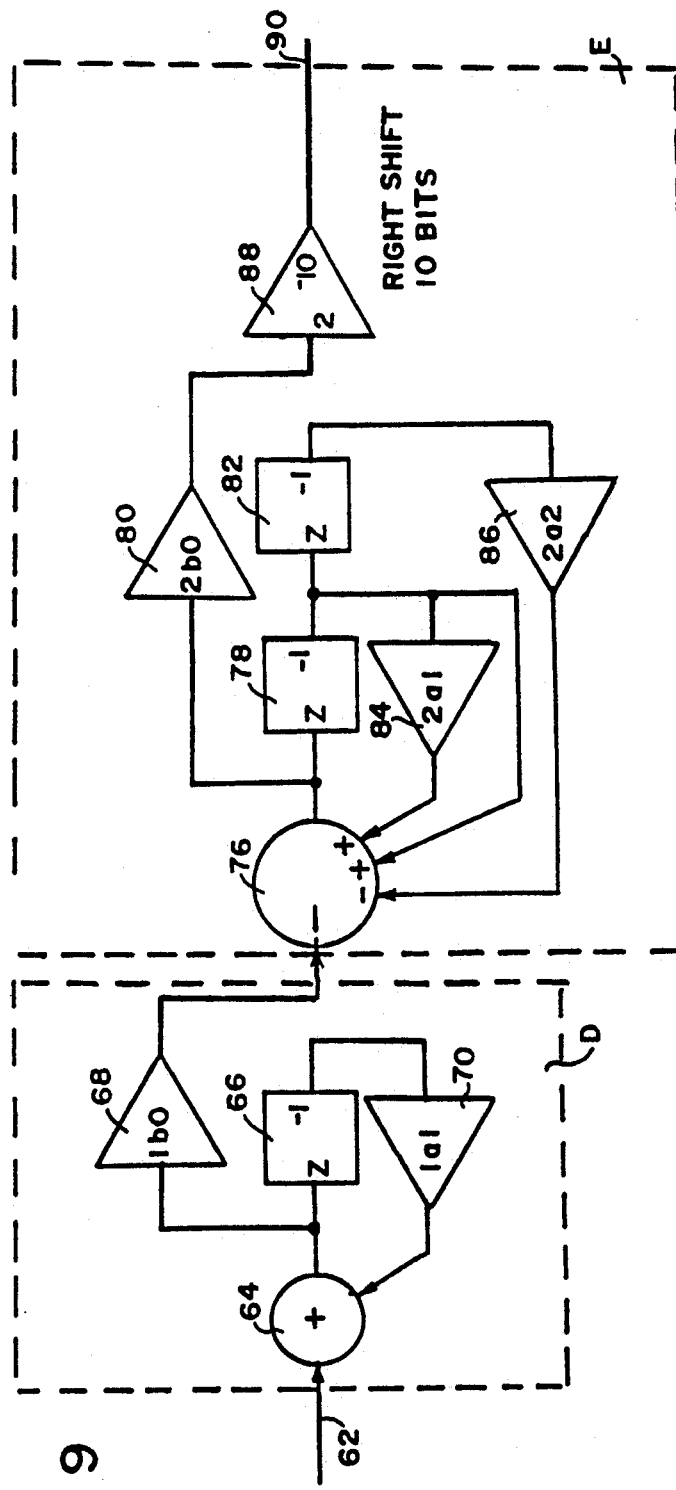
FIG. 9 is a schematic diagram of another embodiment of the IIR low pass filter of the instant invention.
FIG. 10 is a table showing the coefficients for the filter of FIG. 9.
FIG. 11 is a table showing the gains for the two stages of the filter of FIG. 9.

The schematic of the embodiment of the linear phase low pass filter 16 preferably used for visual display such as on a video display system or a chart recorder is shown in detail in FIG. 9. As can be seen with reference to FIG. 9, the linear phase low pass filter 16 is a third order two stage filter. The two stages of the third order embodiment of filter 16 shown in FIG. 9 have been outlined in dotted lines in FIG. 9 and designated with the letters D and E. Stage D is a first order stage because it contains one unit delay labeled 66. Stage E is a second order stage since it contains two unit delays labeled 78 and 82.

In FIG. 9, the first order stage D is placed along the filtering path before the second order stage E in order to produce an output signal from stage D of appropriate gain to prevent the subsequent stage E from being overwhelmed by a high amplitude input ECG signal as explained above in connection with the fifth order three stage embodiment of the invention. Again, as in the description of the fifth order three stage filter, the first and second order stages may be reversed as desired.

Stages D and E have gain block 68 and 80 respectively which multiply the digital signal presented to their inputs by the coefficients $1b_0$ and $2b_0$ respectively. The values of these coefficients, as well as all coefficients used in stages D and E are contained in the table shown in FIG. 10. The gains corresponding to each stage D and E and the overall gain for the filter 16 of this embodiment as shown in FIG. 9 are shown in FIG. 11.

Referring to FIG. 9, the input ECG signal from input 12 is presented to filter input 62 where it is immediately presented to stage D at summer 64. Stage D operates identically to stage A as described above where summer 64 corresponds to summer 24, delay block 66 corresponds to delay block 26, multiplication block 70 corresponds to multiplication block 30, and gain block 68 corresponds to gain block 28. The coefficients for gain block 68 and multiplication block 70 may differ from those used in the embodiment of FIG. 6 and are shown in FIG. 10. In all other ways, stage D operates exactly as does stage A as described above.

The output of gain block 68 is the output of stage D and is presented to stage E at summer 76. Stage E is identical in structure and function to stage C described above where summer 76 corresponds to summer 46, delays 78 and 82 correspond to delays 48 and 52, gain blocks 80 and 88 correspond to gain blocks 50 and 58 and multiplication blocks 84 and 86 correspond to multiplication blocks 54 and 56. The coefficients for multiplication blocks 84 and 86 and gain blocks 80 and 88 are contained in FIG. 10. In stage E, gain block 88 right shifts the output of gain block 80 by 10 bits which has the affect of multiplying the output of gain block 80 by $2^{-10}$ instead of $2^{-16}$ as is done in stage C. In all other ways, stage E functions exactly as does stage C described above. The output of gain block 88 is the output 90 of the filter 16.

The coefficients shown in FIG. 10, when implemented on the two stage third order low pass filter shown in FIG. 9, produce a cutoff frequency for low pass filter 16 of 0.388 Hz and a gain of D.C. of 1.

Figure 13A:
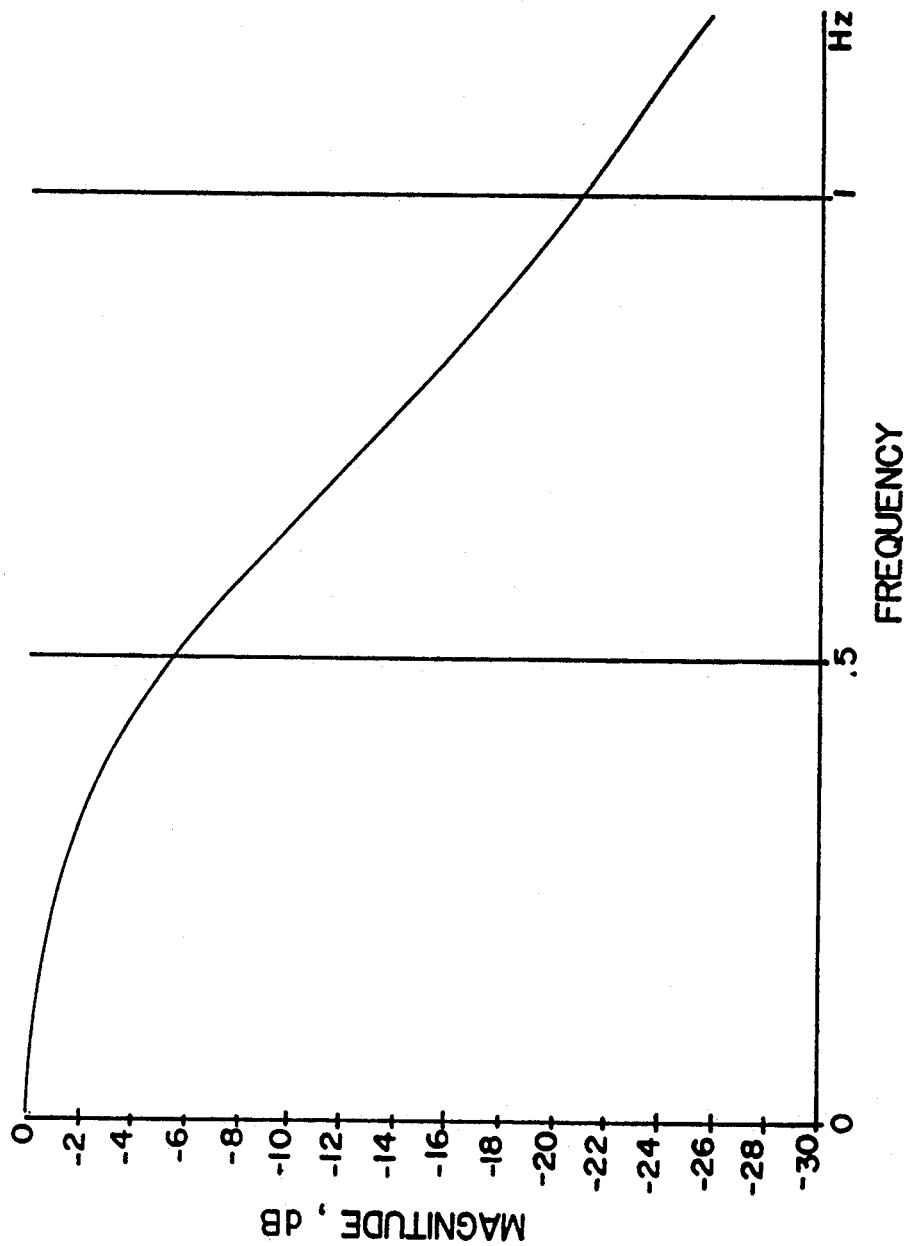
FIG. 13A is a graph showing the magnitude versus frequency for the filter of FIG. 9.
Figure 13B:
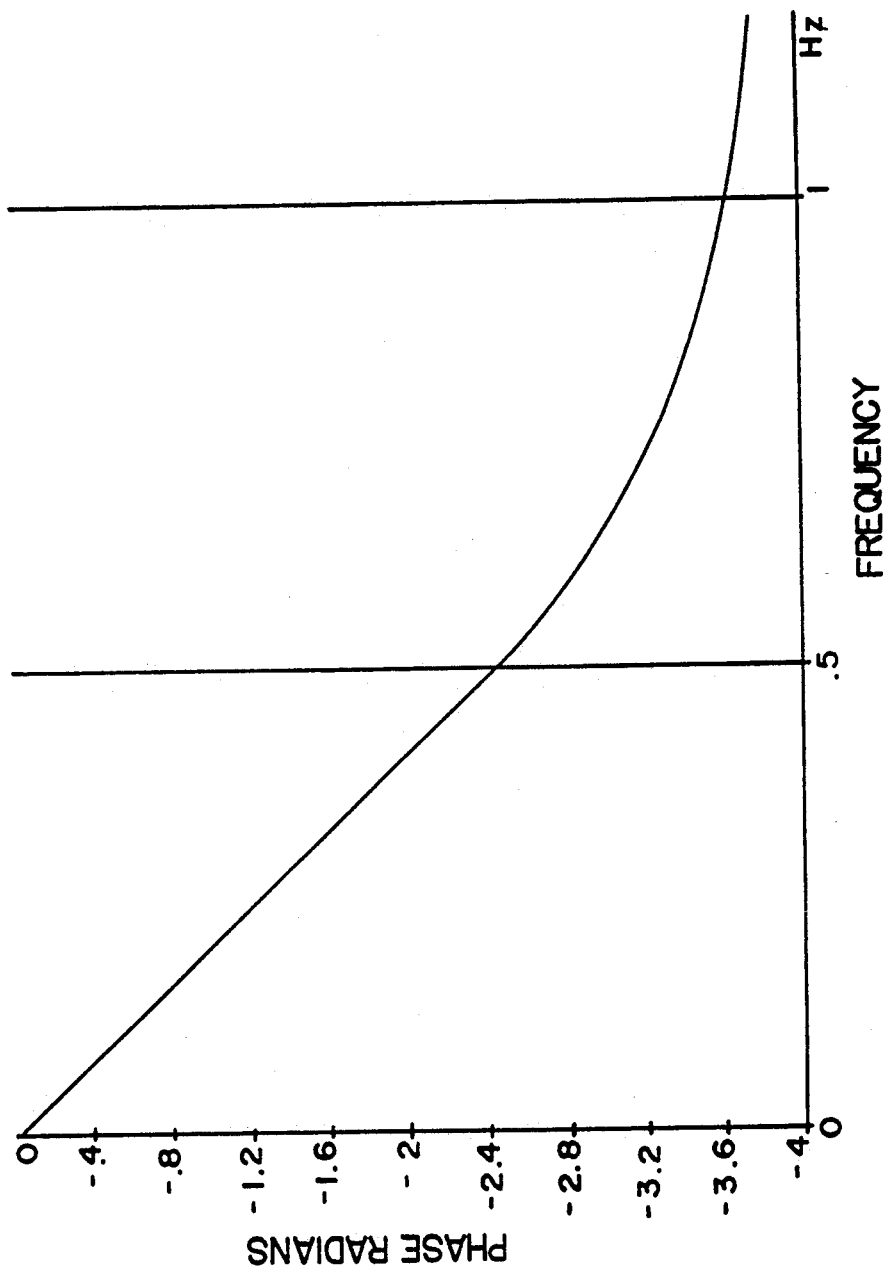
FIG. 13B is a graph showing the phase shift versus frequency for the filter of FIG. 13A.
Figure 13C:
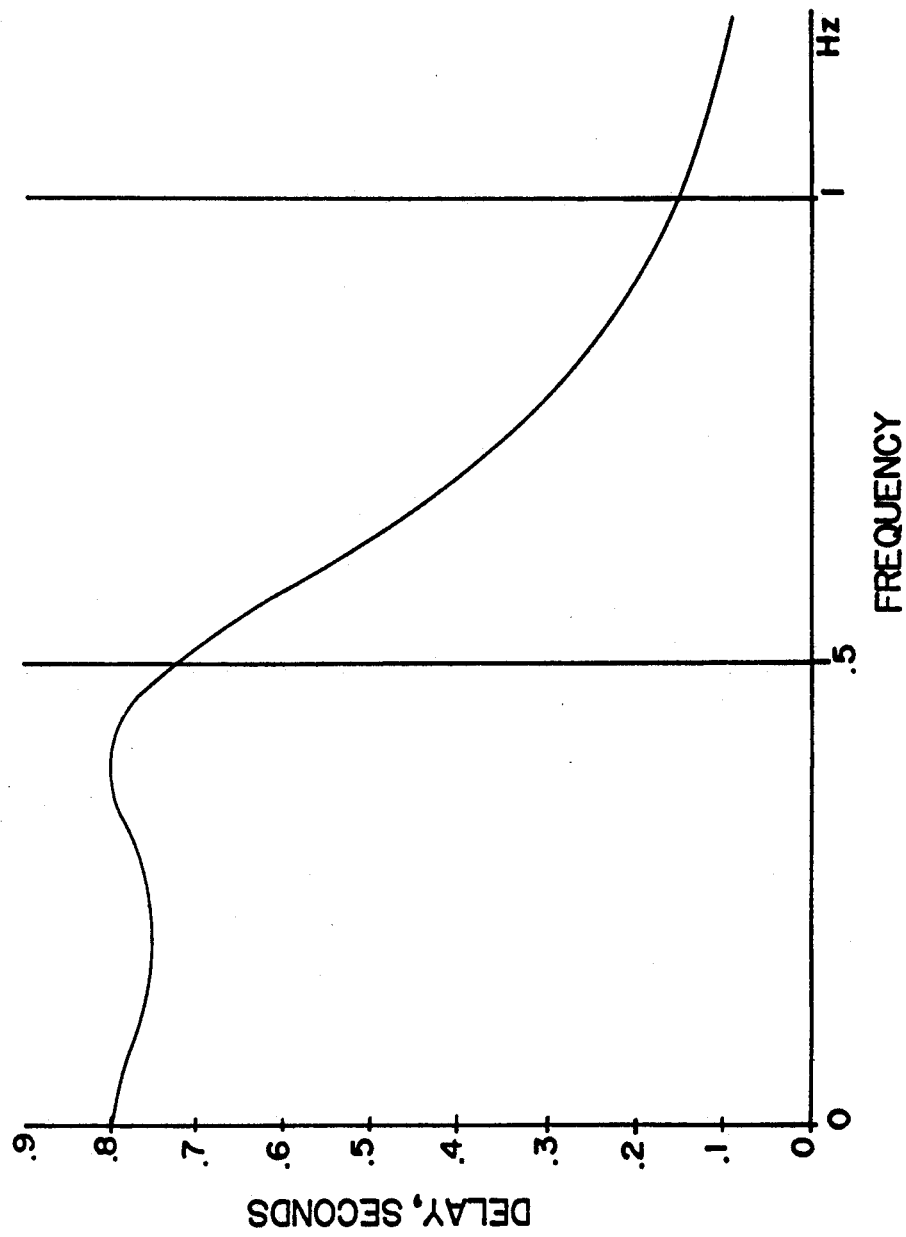
FIG. 13C is a graph showing the delay versus frequency for the filter of FIG. 13A.

A graph showing the amplitude versus frequency of this embodiment of the filter 16 is shown in FIG. 13A. The phase versus the frequency for this embodiment is shown in the graph of FIG. 13B. As can be seen, the phase is linear over the range of 0 Hz to about 0.5 Hz. The corresponding delay of the ECG signal versus frequency is shown in the graph of FIG. 13C. As can be seen, the delay is nearly constant for frequencies below the cutoff frequency of this low pass filter.

Figure 15A:
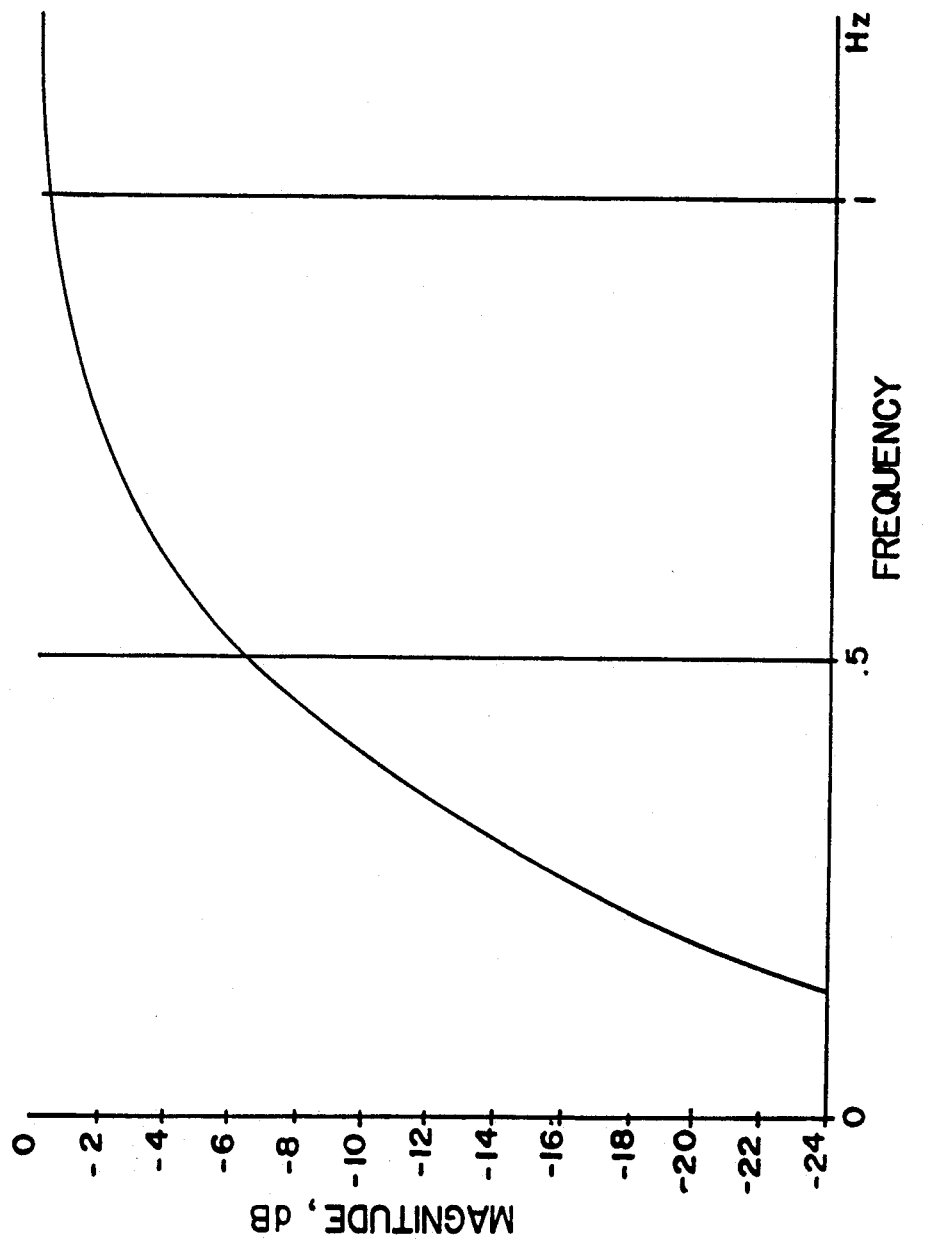
FIG. 15A is a graph showing the magnitude versus frequency for the high pass baseline wander filter of FIG. 5 using the low pass filter of FIG. 9.
Figure 15C:
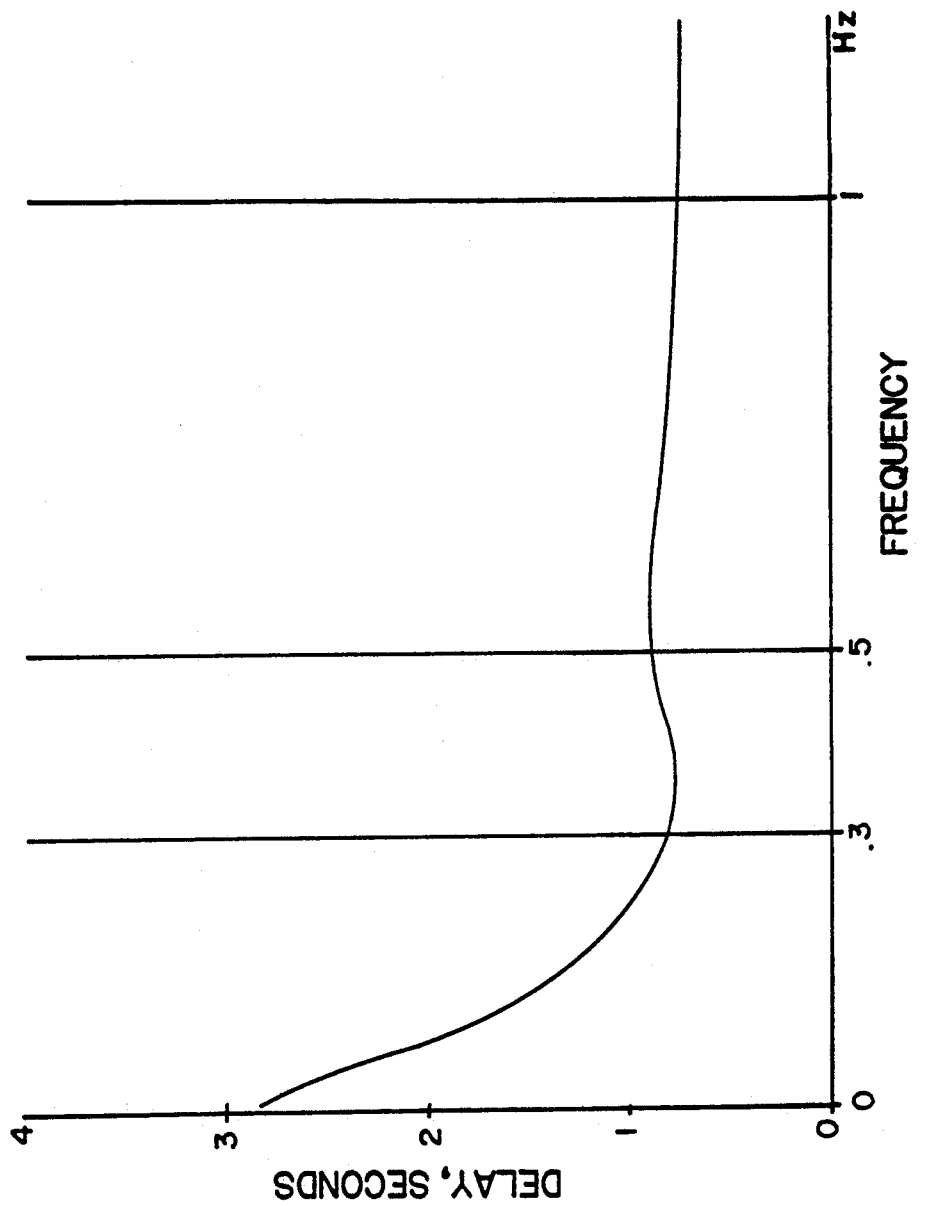
FIG. 15C is a graph showing the delay versus frequency for the high pass baseline wander filter of FIG. 15A.

The output of low pass filter 16 and output 90 is presented to summer 18 where it is subtracted from the output of delay 14 as explained above to produce the high pass filter output at filter output 20. The resulting filter 10 is a high pass filter having a $-3$ dB cutoff frequency of about 0.66 Hz. FIGS. 15B and 15C show the phase shift and delay versus frequency, respectively, for the filter 10 explained above. As can be seen, the phase is linear and the delay constant over the frequencies passed through the filter 10.

The relevant features in designing the low pass filter 16 for both embodiments, as well as other embodiments incorporating the teachings of this invention are as follows:

First, the poles and zeros of a prototype analog filter are looked up in a table of such prototype filters. Then, the analog prototype filter is converted to a desired analog filter corresponding to the desired low pass filter by means of frequency scaling. Thereafter, the analog filter corresponding to the cutoff frequency of interest is converted to a digital filter by means of a matched Z transformation. Although the matched Z transformation has been used in the instant case, it is recognized that many other transformations, such as is well known in the art, could be used to convert the analog filter to a digital filter. Finally, the digital filter is realized as cascaded first and second order stages in the form of direct form II. *Digital Signal Processing* by Alan V. Oppenheim and Ronald W. Schaefer has an excellent discussion on realization of digital filters in Chapter 4 beginning on page 136.

As has been seen, the instant invention includes a low pass filter 16 operated in parallel with the delay 14, both of whose outputs are passed through a summer 18 to produce a high pass filter. The reason that a low pass filter is used in parallel with a delay to create a high pass filter instead of just using a high pass filter is because a high pass filter of conventional Infinite Impulse Response (IIR) design does not have a linear phase response over the entire frequency spectrum of passed frequencies. This leads to a delay in the ECG signal passing through the filter depending on frequency which produces a distorted ECG signal. This is the very problem that is to be avoided in a baseline wander filter. It has been found that an effective way to make a high pass filter with the desired cutoff frequency and the desired linear phase response with its corresponding constant delay regardless of the frequency components of the input ECG signal is to combine the low pass filter and the delay 14 in parallel as taught by the instant invention.

The instant invention has been described in connection with a high pass filter for use in an ECG system for filtering baseline wander from an input ECG signal. Although the instant invention is ideally suited for this purpose, it may also be used as a high pass filter of any type of slowly varying unwanted signal.

The instant invention also has been described in connection with an Infinite Impulse Response (IIR) filter to be used as the linear phase low pas filter 16. As stated, the features of the IIR filter that make it particularly adapted to use with the instant invention is that the low pass IIR filter has a linear phase shift over the frequency spectrum passed through the low pass filter and the IIR filter requires comparatively few computations to be implemented. Although the IIR filter has been described as the preferred embodiment of the linear phase low pass filter 16, it is to be understood that any filter having these two properties, that is linear phase response over the spectrum of frequencies passed through the filter and which has comparatively few computations to be implemented may also be used and are within the scope of the instant invention.

The instant invention has been described in connection with specific embodiments. However, it is to be recognized that the descriptions contained herein have been given by means of example and not for the purpose of limitation. Changes and modifications can be made to the descriptions contained herein and still be within the scope of the invention as claimed. Further, obvious changes and modifications will occur to those skilled in the art.

I claim:

1. A device for removing low frequency signals, including baseline wander signals from an ECG signal comprising:
   a) an ECG input;
   b) means, connected to said ECG input, for attenuating the frequency components of an ECG signal above a preselected cutoff frequency and for passing the frequency components of an ECG signal below said preselected cutoff frequency through said means for attenuating and passing when an ECG signal is presented to said ECG input, said means for attenuating and passing having a linear phase response for those frequency components of an ECG signal passed through said means for attenuating and passing;
   c) means, connected to said ECG input, for delaying the ECG signal presented to said ECG input for a time approximately equal to the time said means for attenuating and passing requires to pass the frequency components of an ECG signal below said preselected cutoff frequency through said means for attenuating and passing; and
   d) means, connected to the output of said means for delaying and to the output of said means for attenuating and passing, for subtracting the output of said means for attenuating and passing from the output of said means for delaying.

2. The device of claim 1 wherein said means for attenuating and passing comprises a linear phase low pass filter.

3. The device of claim 2 wherein said low pass filter is a digital filter.

4. The device of claim 3 wherein said low pass filter is an infinite impulse response filter.

5. The filter of claim 4 wherein said infinite impulse response filter comprises a plurality of filters.

6. The device of claim 5 wherein the plurality of filters of said infinite impulse response filter is three.

7. The device of claim 6 wherein said infinite impulse response filter is a fifth order filter.

8. The device of claim 5 wherein each of said plurality of filters is selected from the group consisting of a first order filter and a second order filter.

9. The device of claim 8 wherein the plurality of filters is three.

10. The device of claim 9 wherein said three filters together are a fifth order filter.

11. The device of claim 10 wherein said electronic memory means are digital electronic memory means.

12. The filter of claim 4 wherein said low pass filter is a variable gain filter.

13. The device of claim 1 wherein said means for delaying includes electronic memory means.

14. The device of claim 1 wherein said means for subtracting includes a summer.

15. A device for removing low frequency signals, including baseline wander signals from an ECG signal comprising:
   a) an ECG input;
   b) means, connected to said ECG input, for attenuating the frequency components of an ECG signal above a preselected cutoff frequency and for passing the frequency components of an ECG signal below said preselected cutoff frequency through said means for attenuating and passing when an ECG signal is presented to said ECG input, said means for attenuating and passing having a linear phase response for those frequency components of an ECG signal passed through said means for attenuating and passing, said means for attenuating and passing comprising a linear phase low pass filter;
   c) means, connected to said ECG input, for delaying the ECG signal presented to said ECG input for a time approximately equal to the time said means for attenuating and passing requires to pass the frequency components of an ECG signal below said preselected cutoff frequency through said means for attenuating and passing, said means for delaying including electronic memory means; and
   d) means, connected to the output of said means for delaying and to the output of said means for attenuating and passing, for subtracting the output of said means for attenuating and passing from the output of said means for delaying, said means for subtracting including a summer.

16. A device for removing low frequency signals, including baseline wander signals from an ECG signal comprising:
   a) an ECG input;

b) means, connected to said ECG input, for attenuating the frequency components of an ECG signal above a preselected cutoff frequency and for passing the frequency components of an ECG signal below said preselected cutoff frequency through said means for attenuating and passing when an ECG signal is presented to said ECG input, said means for attenuating and passing having a linear phase response for those frequency components of an ECG signal passed through said means for attenuating and passing, said means for attenuating and passing comprising a digital infinite impulse response linear phase low pass filter;

c) means, connected to said ECG input, for delaying the ECG signal presented to said ECG input for a time approximately equal to the time said means for attenuating and passing requires to pass the frequency components of an ECG signal below said preselected cutoff frequency through said means for attenuating and passing, said means for delaying including digital electronic memory means; and d) means, connected to the output of said means for delaying and to the output of said means for attenuating and passing, for subtracting the output of said means for attenuating and passing from the output of said means for delaying, said means for subtracting including a summer.

17. The filter of claim 16 wherein said infinite impulse response filter comprises a plurality of filters.

18. The device of claim 17 wherein said digital infinite impulse response linear phase low pass filter is a fifth order filter.

19. The device of claim 17 wherein said digital infinite impulse response linear phase low pass filter is a third order filter.

20. A method for removing low frequency signals, including baseline wander signals from an ECG signal comprising the steps of:

a) simultaneously presenting an ECG signal to a linear phase low pass filter and a delay means;

b) attenuating the frequency components of the ECG signal above a predetermined cutoff frequency presented to said low pass filter;

c) delaying the ECG signal presented to said delay means for a time approximately equal to the time required by said low pass filter to pass the ECG signal through said low pass filter; and d) subtracting the ECG signal passed through said low pass filter from the signal delayed by said delay means.

* * * * *

UNITED STATES PATENT AND TRADEMARK OFFICE
CERTIFICATE OF CORRECTION

PATENT NO. : 5,269,313
DATED : Dec. 14, 1993
INVENTOR(S) : Victor M. DePinto

It is certified that error appears in the above-indentified patent and that said Letters Patent is hereby corrected as shown below:

On the title page, item [73],

Assignee: Quinton Instrument Company

Signed and Sealed this

Seventeenth Day of March, 1998

Attest:

Attesting Officer

BRUCE LEHMAN

Commissioner of Patents and Trademarks